US009522867B2

(12) United States Patent
Yoshida et al.

(10) Patent No.: US 9,522,867 B2
(45) Date of Patent: Dec. 20, 2016

(54) (METH)ACRYLIC ACID PRODUCTION METHOD, AND, HYDROPHILIC RESIN PRODUCTION METHOD

(71) Applicant: NIPPON SHOKUBAI CO., LTD., Osaka-shi, Osaka (JP)

(72) Inventors: Hiroshi Yoshida, Osaka (JP); Hisashi Kamei, Osaka (JP); Naomichi Haginiwa, Osaka (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 14/409,349

(22) PCT Filed: Jun. 21, 2013

(86) PCT No.: PCT/JP2013/067065
§ 371 (c)(1),
(2) Date: Dec. 18, 2014

(87) PCT Pub. No.: WO2014/002886
PCT Pub. Date: Jan. 3, 2014

(65) Prior Publication Data
US 2015/0175517 A1 Jun. 25, 2015

(30) Foreign Application Priority Data

| Jun. 27, 2012 | (JP) | 2012-144635 |
| Jun. 27, 2012 | (JP) | 2012-144636 |
| Jan. 17, 2013 | (JP) | 2013-006619 |
| Jan. 17, 2013 | (JP) | 2013-006620 |
| Jan. 17, 2013 | (JP) | 2013-006621 |

(51) Int. Cl.
*B01J 27/182* (2006.01)
*B01J 27/28* (2006.01)
*C07C 51/353* (2006.01)
*C07C 51/377* (2006.01)
*C08F 20/06* (2006.01)
*C08G 63/06* (2006.01)
*C12P 7/40* (2006.01)
*B01J 29/90* (2006.01)

(52) U.S. Cl.
CPC ............ *C07C 51/377* (2013.01); *B01J 27/182* (2013.01); *B01J 27/285* (2013.01); *C07C 51/353* (2013.01); *C08F 20/06* (2013.01); *C08G 63/06* (2013.01); *C12P 7/40* (2013.01); *B01J 29/90* (2013.01); *Y02P 20/582* (2015.11); *Y02P 20/584* (2015.11)

(58) Field of Classification Search
CPC ......... B01J 27/182; B01J 27/285; B01J 29/90; C07C 51/353; C07C 51/377; C08G 63/06; C12P 7/40; C08F 20/06; Y02P 20/582; Y02P 20/584
See application file for complete search history.

(56) References Cited

U.S. PATENT DOCUMENTS

| 3,002,017 | A | * | 9/1961 | Wearsch | ................. C07C 51/09 |
| | | | | | 422/198 |
| 6,444,744 | B1 | * | 9/2002 | Fujimaru | ................. A61L 15/24 |
| | | | | | 524/556 |
| 6,852,517 | B1 | * | 2/2005 | Suthers | ................. C12N 9/0008 |
| | | | | | 435/135 |
| 6,897,338 | B2 | | 5/2005 | Zhong et al. | |
| 7,166,743 | B2 | | 1/2007 | Zhong et al. | |
| 7,714,097 | B2 | * | 5/2010 | Zhang | ................... C08G 63/08 |
| | | | | | 525/450 |
| 2003/0158441 | A1 | | 8/2003 | Zhong et al. | |
| 2005/0182235 | A1 | | 8/2005 | Zhong et al. | |
| 2005/0221457 | A1 | | 10/2005 | Tsobanakis et al. | |
| 2005/0222458 | A1 | | 10/2005 | Craciun et al. | |
| 2007/0015936 | A1 | | 1/2007 | Meng et al. | |
| 2007/0219397 | A1 | | 9/2007 | Holladay et al. | |
| 2009/0023006 | A1 | | 1/2009 | Bub et al. | |
| 2011/0105791 | A1 | | 5/2011 | Kuppinger et al. | |
| 2012/0041232 | A1 | | 2/2012 | Lynch | |
| 2013/0281649 | A1 | | 10/2013 | Yoshida et al. | |

FOREIGN PATENT DOCUMENTS

| JP | 2000-159724 | 6/2000 |
| JP | 2004-532855 | 10/2004 |
| JP | 2006-518766 | 8/2006 |

(Continued)

*Primary Examiner* — Fereydoun G Sajjadi
*Assistant Examiner* — Mark Luderer
(74) *Attorney, Agent, or Firm* — Hamre, Schumann, Mueller & Larson P.C.

(57) ABSTRACT

The present invention provides a method for producing (meth)acrylic acid, which achieves enhanced productivity or a reduced amount of a catalyst in production of (meth) acrylic acid from 3-hydroxycarboxylic acid, and enables stable production of (meth)acrylic acid at low cost. The method is a method for producing (meth)acrylic acid using 3-hydroxycarboxylic acid as a starting material, the method including a polymerization step of polymerizing 3-hydroxycarboxylic acid to generate a composition containing a 3-hydroxycarboxylic acid polymer, and a step of generating (meth)acrylic acid from the composition containing the 3-hydroxycarboxylic acid polymer, the 3-hydroxycarboxylic acid polymer obtained in the polymerization step including trimer or higher order units, the trimer or higher order units constituting 3% by mass or more of a total of 100% by mass of the 3-hydroxycarboxylic acid and the 3-hydroxycarboxylic acid polymer.

19 Claims, 9 Drawing Sheets

(56) References Cited

FOREIGN PATENT DOCUMENTS

| | | |
|---|---|---|
| JP | 2011-225533 | 11/2011 |
| JP | 2012-077014 | 4/2012 |
| WO | 02/090312 | 11/2002 |
| WO | 2005/095320 | 10/2005 |
| WO | 2007/106100 | 9/2007 |
| WO | 2011/002892 | 1/2011 |
| WO | 2011/100608 | 8/2011 |
| WO | 2012/091114 | 7/2012 |

* cited by examiner

3HP → Acrylic acid (One-stage dehydration reaction)

# (METH)ACRYLIC ACID PRODUCTION METHOD, AND, HYDROPHILIC RESIN PRODUCTION METHOD

TECHNICAL FIELD

The present invention relates to a method for producing (meth)acrylic acid from a material composition containing 3-hydroxycarboxylic acid or a polymer thereof, and a method for producing a hydrophilic resin.

BACKGROUND ART (Meth)acrylic acid has been widely used industrially as a starting material of an acrylic resin or a hydrophilic resin. A typical method for producing (meth)acrylic acid is a two-step oxidation method of oxidizing propylene or isobutylene, which are materials derived from fossil resources, into acrolein or methacrolein in vapor in the presence of an oxide catalyst using a fixed-bed multi-tubular continuous reactor, and further oxidizing the product in vapor. Such (meth) acrylic acid, however, has been desired to be produced from a renewable resource, not from a fossil resource.

Now, economical production of (meth)acrylic acid on a commercial scale using a renewable resource such as biomass has been tried. Examples of the method for producing (meth)acrylic acid from biomass include a method of obtaining a saccharide from a natural product (e.g. agricultural product) or by decomposing cellulose or the like substance; fermenting the saccharide to obtain a 3-hydroxycarboxylic acid species such as 3-hydroxypropionic acid (hereinafter, also referred to as 3HP) or 3-hydroxyisobutyric acid; and dehydrating the 3-hydroxycarboxylic acid species.

Patent Literature documents 1 to 7 disclose conventional methods for generating (meth)acrylic acid and methods related to these methods. Patent Literature documents 8 to 10 disclose a method for generating (meth)acrylic acid by pyrolyzing a 3HP polymer by a specific method.

CITATION LIST

Patent Literature

Patent Literature 1: WO 2005/095320
Patent Literature 2: WO 2007/106100
Patent Literature 3: JP 2006-518766 T
Patent Literature 4: JP 2000-159724 A
Patent Literature 5: WO 2012/091114
Patent Literature 6: JP 2004-532855 T
Patent Literature 7: WO 2011/002892
Patent Literature 8: U.S. Pat. No. 7,166,743 B
Patent Literature 9: U.S. Pat. No. 6,897,338 B
Patent Literature 10: WO 2011/100608

SUMMARY OF INVENTION

Technical Problem

An object of the present invention is to provide a method for producing (meth)acrylic acid which can stably produce (meth)acrylic acid with high productivity. Another object of the present invention is to provide a suitable method for producing a hydrophilic resin using the (meth)acrylic acid obtained by the above method. Yet another object of the present invention is to provide a composition that contains (meth)acrylic acid or a hydrophilic resin and has a reduced amount of a nitrogen-containing compound.

A 3-hydroxycarboxylic acid is a possible starting material in the method for producing (meth)acrylic acid. First, the object of the first aspect of the present invention relating to the method for producing (meth)acrylic acid using 3-hydroxycarboxylic acid as a starting material is described.

Patent Literature documents 1 and 2 disclose production of acrylic acid which includes a reaction involving dimers and oligomers as one of the reaction stages. Patent Literature documents 3 and 4 disclose synthesis of 3HP by hydration of acrylic acid, for example.

Patent Literature document 5 discloses a method for producing acrylic acid and/or an ester thereof and a polymer thereof. Patent Literature documents 6 and 7 relate to purification of 3HP, and so on. The inventions of Patent Literature documents 8 to 10 relate to production of acrylic acid using a polymer called polyhydroxyalkanoate (hereinafter, also referred to as PHA) as a starting material. These documents do not disclose production of (meth)acrylic acid using a monomer such as 3HP as a starting material.

The methods described in Patent Literature documents 1 to 10 can still be improved in enhancement of the productivity or in reduction in the amount of the catalyst for production of (meth)acrylic acid using 3-hydroxycarboxylic acid as a starting material. Also, the methods of Patent Literature documents 1 to 10 are insufficient about stable production of (meth)acrylic acid at low cost, and can therefore be further improved.

Accordingly, the object of the first aspect of the present invention is to provide a method for producing (meth)acrylic acid which achieves enhanced productivity or reduction in the amount of a catalyst for production of (meth)acrylic acid from 3-hydroxycarboxylic acid, and enables stable production of the (meth)acrylic acid at low cost.

In other words, the object of the first aspect of the present invention is to solve the problems that the formulation of an aqueous solution of 3-hydroxycarboxylic acid being a monomer is not stable due to oligomerization with time, and thus the solution is unsuitable for industrial production; and in the case of using 3-hydroxycarboxylic acid being a monomer as a starting material, the productivity in the dehydration reaction is insufficient.

Subsequently, the objects of the second and third aspects of the present invention relating to the method for producing (meth)acrylic acid using a composition containing a 3-hydroxycarboxylic acid polymer are described.

The present inventors have found problems in Patent Literatures 1 and 2 that polymers such as oligomers deposit to the inner surface of a reactor or the like instruments to eventually cause clogging in the reactor or the like instruments, making it difficult to achieve long-term, stable production, and that the polymers deposited cover the surface of the catalyst to decrease the catalytic activity, decreasing the yield of the (meth)acrylic acid.

Also, the methods of Patent Literature documents 3 to 7 do not teach production of (meth)acrylic acid using a composition containing a 3-hydroxycarboxylic acid polymer as a starting material.

PHA used in Patent Literature documents 8 to 10 is typically in the solid state which complicates the handling of PHA and gives low thermal conductivity to PHA, and thus brings about low decomposition efficiency under heat. In order to facilitate the handling, methods such as suspending the PHA in water to handle the PHA in the slurry state, and dissolving the PHA in an organic solvent to handle the PHA in the state of a solution. These methods, however, have problems that the energy required for heating is excessive, and a step of recovering the solvent is required. Furthermore, PHA having a high molecular weight requires a certain length of residence time for decomposition, and tends to undergo reactions such as denaturation due to heating during the residence time, leading to a decrease in the yield of acrylic acid. Here, the denatured heavy component causes clogging in the reactor or a decrease in the heat conductivity. Accordingly, it has been difficult to achieve long-term, stable production with a high yield.

As described above, the methods described in Patent Literature documents 1 to 10 can still be improved because these are insufficient in achieving low cost and suppression of clogging in the reactor or the like instruments or a decrease in the catalytic activity for production of (meth)acrylic acid using a composition containing a 3-hydroxycarboxylic acid polymer, and achieving long-term, stable production of (meth)acrylic acid with a high yield.

Meanwhile, in order to maintain the formulation of the composition with a large number of monomers or dimers of 3-hydroxycarboxylic acid, i.e., with a low degree of polymerization, the concentration of water in the composition needs to be high. In this case, the yield of the (meth)acrylic acid is relatively high, but a large amount of energy is required for evaporation of the composition in the vapor phase reaction. Also, the low concentration of the 3-hydroxycarboxylic acid units raises a problem of low productivity, which leads to the need for a large device, requiring excessive investment.

Also, the object of the second aspect of the present invention is to provide a method for producing (meth)acrylic acid which achieves low cost and suppression of clogging in the reactor or the like instruments and a decrease in the catalytic activity for production of (meth)acrylic acid using a composition containing a 3-hydroxycarboxylic acid polymer, and achieves long-term, stable production of (meth)acrylic acid with a high yield.

In other words, the object of the second aspect of the present invention is to solve the problem that the composition containing a 3-hydroxycarboxylic acid polymer for production of (meth)acrylic acid may exhibit different properties such as high utility and a low yield of (meth)acrylic acid, depending on its formulation.

The object of the third aspect of the present invention is to provide a method for producing (meth)acrylic acid which can suppress clogging in the reactor or the like instruments and a decrease in the catalytic activity in production of (meth)acrylic acid using a composition containing a 3-hydroxycarboxylic acid polymer, and can achieve long-term, stable production of (meth)acrylic acid with a high yield.

In other words, the object of the third aspect of the present invention is to solve the problem that use of a composition containing a 3-hydroxycarboxylic acid polymer without any change in the dehydration reaction may cause clogging or a decrease in the catalytic activity.

Solution to Problem

The present inventors have made various studies on the method for producing (meth)acrylic acid to achieve the object of the first aspect of the present invention, and focused on a method for producing (meth)acrylic acid using 3-hydroxycarboxylic acid as a starting material. As a result, the present inventors have arrived at the following findings.

First, a monomer solution of 3-hydroxycarboxylic acid is oligomerized with time, and thus has an unstable formulation, which leads to an unstable reaction for obtaining (meth)acrylic acid to vary the yield. Consequently, the formulation may not be stable in the purification step, and thus the qualities may be varied. The present inventors, however, have found that by a method which allows the oligomerization of 3-hydroxycarboxylic acid to proceed sufficiently to specify the formulation of the polymers such as oligomers, the formulation of the oligomer solution in the present invention is relatively stable (close to the equilibrium state) and the reaction thereof is stable so that the solution is industrially suitable. The method has also been found to eliminate the need for operations and equipment for stabilizing the reaction, thereby reducing the cost. Here, the present inventors have also found that the stabilization of the formulation results in stabilization of the formulation and qualities of the (meth)acrylic acid as a product, providing great industrial advantages.

The present inventors have also found that by allowing oligomerization of 3-hydroxycarboxylic acid to proceed sufficiently to specify the formulation of the polymers such as oligomers, and then generating (meth)acrylic acid from the composition containing a 3-hydroxycarboxylic acid polymer through a dehydration reaction, the load in the dehydration reaction can be reduced, so that the productivity can be enhanced or the amount of the catalyst is reduced. That is, the load in the whole dehydration reaction can be reduced compared to the case of producing (meth)acrylic acid through a one-stage dehydration reaction of 3-hydroxycarboxylic acid when the oligomerization, which is one of the dehydration reactions, is allowed to proceed sufficiently, and then the dehydration of generating (meth)acrylic acid from the composition containing a 3-hydroxycarboxylic acid polymer is performed. Here, none of the Patent Literature documents discloses specification of the formulation of the polymers such as oligomers as in the case of the present invention.

In the case of producing (meth)acrylic acid from a renewable resource as described above, for example in the case that the method for producing (meth)acrylic acid includes a fermentation step which generates 3-hydroxycarboxylic acid as a starting material, fermented mash of 3-hydroxycarboxylic acid itself cannot be used for the dehydration reaction for obtaining (meth)acrylic acid and is preferably purified in advance because the fermented mash commonly has a concentration of the 3-hydroxycarboxylic acid of as low as about 10%, and contains a large amount of impurities such as bacterial cells, protein, glucose, and salts.

3-Hydroxycarboxylic acid is likely to be oligomerized under heat in the purification and condensation step, and highly concentrated 3-hydroxycarboxylic acid may be oligomerized even at room temperature.

Here, the present inventors have found that allowing the oligomerization to proceed sufficiently to adjust the formulation of the polymers such as oligomers to a specific formulation in such a purification and condensation step enables stable production of (meth)acrylic acid with high productivity, and is thus suitable.

Furthermore, the present inventors have found that the cost for evaporation increases high in a reaction involving evaporation of starting materials and products if the concentration of 3-hydroxycarboxylic acid is low, and thus the concentration of 3-hydroxycarboxylic acid is preferably reasonably high, not only in the case that the composition contains a renewable resource as a starting material but also in the case that the step of generating (meth)acrylic acid from a composition containing a 3-hydroxycarboxylic acid polymer includes the step of performing a reaction that involves evaporation of the starting materials and generated products.

The inventions described in Patent Literature documents 1 and 2, differently from the present invention, are not based on the concept of producing a specific oligomer using 3-hydroxycarboxylic acid and thereby suitably producing (meth)acrylic acid. Meanwhile, the invention described in Patent Literature document 5 is based on the concept of minimizing the amount of oligomers of hydroxypropionic acid to suitably evaporate hydroxypropionic acid. The present invention, differently from the invention described in Patent Literature document 5, is based on the concept of actively producing an oligomer of 3-hydroxycarboxylic acid and utilizing the oligomer. The inventions described in Patent Literature documents 8 to 10 are not based on the concept of suitably producing (meth)acrylic acid through production of a specific oligomer in production of (meth) acrylic acid using a monomer of 3-hydroxycarboxylic acid as a starting material, and in this point, the present invention is different from these inventions.

That is, the present inventors have made various studies to achieve the object of the first aspect of the present invention, and have found that the first object can be achieved by allowing oligomerization of 3-hydroxycarboxylic acid to proceed sufficiently in production of (meth) acrylic acid using the 3-hydroxycarboxylic acid as a starting material, so that trimer or higher order units constitute 3% by mass or more of a total of 100% by mass of the 3-hydroxycarboxylic acid and the 3-hydroxycarboxylic acid polymer. When the oligomerization is allowed to proceed to such an extent in, for example, the purification and condensation step, and then (meth)acrylic acid is generated from a composition containing a 3-hydroxycarboxylic acid polymer, variations of the reaction results and product qualities can be reduced as a result of stabilization of the material formulation, and also the load in the whole dehydration reaction can be reduced, so that the productivity of the (meth)acrylic acid can be increased or the amount of the catalyst can be reduced. Also, the (meth)acrylic acid can be stably produced at low cost.

Also, the present inventors have made various studies to achieve the object of the second aspect of the present invention, and have found that, in production of (meth) acrylic acid using 3-hydroxycarboxylic acid as a starting material, heating the material composition containing a specific amount of trimer to eicosamer of the 3-hydroxycarboxylic acid polymer achieves low cost and suppression of clogging in the reactor or the like instruments and a decrease in the catalytic activity, and also achieves long-term, stable production of (meth)acrylic acid with a high yield.

The present inventors have also made various studies to achieve the object of the third aspect of the present invention, and have found that clogging in the reactor or the like instruments and a decrease in the catalytic activity are suppressed, and long-term, stable production of (meth) acrylic acid can be achieved with a high yield by performing the production of (meth)acrylic acid under the following conditions. That is, in production of (meth)acrylic acid using 3-hydroxycarboxylic acid as a starting material, the production includes a decomposition step of generating decomposed products of the polymer and a dehydration step of generating (meth)acrylic acid by bringing the decomposed products into contact with a catalyst for dehydration, i.e., a dehydration catalyst.

These methods can be used in any suitable combination, and such a combined method is also a preferred embodiment of the method of the present invention.

Furthermore, the present inventors have found that a hydrophilic resin such as a water-absorbing resin and a water-soluble resin can be produced preferably using (meth) acrylic acid obtained by any one of the above methods. Thereby, the present invention has been completed.

There are a variety of possibilities for the technique for the purification and condensation step (e.g., membrane separation, distillation and evaporation, electrodialysis, extraction), and thus the present inventors are still making studies.

That is, the present invention relates to a method for producing (meth)acrylic acid using 3-hydroxycarboxylic acid as a starting material, the method including a polymerization step of polymerizing 3-hydroxycarboxylic acid to generate a composition containing a 3-hydroxycarboxylic acid polymer, and a step of generating (meth)acrylic acid from the composition containing the 3-hydroxycarboxylic acid polymer, the 3-hydroxycarboxylic acid polymer obtained in the polymerization step including trimer or higher order units, the trimer or higher order units constituting 3% by mass or more of a total of 100% by mass of the 3-hydroxycarboxylic acid and the 3-hydroxycarboxylic acid polymer. The technical concept relating to this production method herein is also referred to as the first aspect of the present invention.

The present invention also relates to a method for producing (meth)acrylic acid using 3-hydroxycarboxylic acid as a starting material, the method including a polymerization step of polymerizing 3-hydroxycarboxylic acid to generate a composition containing a 3-hydroxycarboxylic acid polymer, and a step of generating (meth)acrylic acid from the composition containing the 3-hydroxycarboxylic acid polymer, wherein trimer to eicosamer in the 3-hydroxycarboxylic acid polymer constitute 10% by mass or more of a total of 100% by mass of the 3-hydroxycarboxylic acid and the 3-hydroxycarboxylic acid polymer, and the (meth)acrylic acid generation step includes heating the material composition to generate (meth)acrylic acid. The technical concept relating to this production method herein is also referred to as the second aspect of the present invention.

Furthermore, the present invention also relates to a method for producing (meth)acrylic acid using 3-hydroxycarboxylic acid as a starting material, the method including a polymerization step of polymerizing 3-hydroxycarboxylic acid to generate a composition containing a 3-hydroxycarboxylic acid polymer, and a step of generating (meth)acrylic acid from the composition containing the 3-hydroxycarboxylic acid polymer, the (meth)acrylic acid generation step including (a) a decomposition step of generating a decomposed product of the 3-hydroxycarboxylic acid polymer, and (b) a dehydration step of generating (meth)acrylic acid by bringing the decomposed product into contact with a dehydration catalyst. The technical concept relating to this production method herein is also referred to as the third aspect of the present invention.

Here, since the technical concepts of the second aspect of the present invention and the third aspect of the present invention described above are to use a 3-hydroxycarboxylic acid polymer to solve the problems relating to the method for producing (meth)acrylic acid, the polymerization step of generating a composition containing a 3-hydroxycarboxylic acid polymer through polymerization of the 3-hydroxycarboxylic acid is not always necessary.

That is, the present invention also relates to a method for producing (meth)acrylic acid from a material composition containing a 3-hydroxycarboxylic acid polymer, wherein trimer to eicosamer in the 3-hydroxycarboxylic acid polymer constitute 10% by mass or more of a total of 100% by mass of the 3-hydroxycarboxylic acid and the 3-hydroxycarboxylic acid polymer, and the method includes heating the composition to generate (meth)acrylic acid.

The present invention also relates to a method for generating (meth)acrylic acid from a material composition containing a 3-hydroxycarboxylic acid polymer, which includes (a) a decomposition step of generating a decomposed product of the 3-hydroxycarboxylic acid polymer, and (b) a dehydration step of generating (meth)acrylic acid by bringing the decomposed product into contact with a dehydration catalyst.

The present invention also relates to a composition containing (meth)acrylic acid obtained by the production method of the present invention, the composition containing a nitrogen-containing compound that gives an amount of nitrogen of 80 ppm by mass or less based on the (meth)acrylic acid.

The present invention also relates to a method for producing a hydrophilic resin using 3-hydroxycarboxylic acid as a starting material, the method including: a first polymerization step of polymerizing 3-hydroxycarboxylic acid to generate a composition containing a 3-hydroxycarboxylic acid polymer; a step of generating (meth)acrylic acid from the composition containing the 3-hydroxycarboxylic acid polymer; and a second polymerization step of polymerizing a monomeric component containing the (meth)acrylic acid to generate a hydrophilic resin, the 3-hydroxycarboxylic acid polymer obtained in the first polymerization step including trimer or higher order units, the trimer or higher order units constituting 3% by mass or more of a total of 100% by mass of the 3-hydroxycarboxylic acid and the 3-hydroxycarboxylic acid polymer. The technical concept relating to this production method corresponds to the first aspect of the present invention. Here, the monomeric component containing (meth)acrylic acid may be any monomeric component containing (meth)acrylic acid obtained by the production method of the present invention, and may further contain other monomer(s) according to need. Here, the monomeric component may be a component contained in a composition containing materials such as a crosslinking agent and a polymerization initiator when the polymerization is performed.

The present invention also relates to a method for producing a hydrophilic resin using 3-hydroxycarboxylic acid as a starting material, the method including: a first polymerization step of polymerizing 3-hydroxycarboxylic acid to generate a composition containing a 3-hydroxycarboxylic acid polymer; a step of generating (meth)acrylic acid from the composition containing the 3-hydroxycarboxylic acid polymer; and a second polymerization step of polymerizing a monomeric component containing the (meth)acrylic acid to generate a hydrophilic resin, wherein trimer to eicosamer in the 3-hydroxycarboxylic acid polymer obtained in the first polymerization step constitute 10% by mass or more of a total of 100% by mass of the 3-hydroxycarboxylic acid and the 3-hydroxycarboxylic acid polymer, and the method includes heating the composition to generate (meth)acrylic acid. The technical concept relating to this production method corresponds to the second aspect of the present invention.

The present invention also relates to a method for producing a hydrophilic resin using 3-hydroxycarboxylic acid as a starting material, the method including: a first polymerization step of polymerizing 3-hydroxycarboxylic acid to generate a composition containing a 3-hydroxycarboxylic acid polymer, a step of generating (meth)acrylic acid from the composition containing the 3-hydroxycarboxylic acid polymer, and a second polymerization step of polymerizing a monomeric component containing the (meth)acrylic acid to generate a hydrophilic resin, the (meth)acrylic acid generation step comprising (a) a decomposition step of generating a decomposed product of the 3-hydroxycarboxylic acid polymer, and (b) a dehydration step of generating (meth)acrylic acid by bringing the decomposed product into contact with a dehydration catalyst. The technical concept relating to this production method corresponds to the third aspect of the present invention.

As described above, in the second aspect of the present invention and the third aspect of the present invention, the polymerization step of generating a composition containing a 3-hydroxycarboxylic acid polymer through polymerization of the 3-hydroxycarboxylic acid is not always necessary.

That is, the present invention also relates to a method for producing a hydrophilic resin from a material composition containing a 3-hydroxycarboxylic acid polymer, the method including a step of generating (meth)acrylic acid from a material composition containing a 3-hydroxycarboxylic acid polymer, and a polymerization step of generating a hydrophilic resin by polymerizing a monomeric component containing the (meth)acrylic acid, wherein trimer to eicosamer in the 3-hydroxycarboxylic acid polymer constitute 10% by mass or more of a total of 100% by mass of the 3-hydroxycarboxylic acid and the 3-hydroxycarboxylic acid polymer, and the method includes a step of heating the composition to generate (meth)acrylic acid.

The present invention also relates to a method for producing a hydrophilic resin from a material composition containing a 3-hydroxycarboxylic acid polymer, the method including a step of generating (meth)acrylic acid from a material composition containing a 3-hydroxycarboxylic acid polymer, and a polymerization step of generating a hydrophilic resin by polymerizing a monomeric component containing the (meth)acrylic acid, the (meth)acrylic acid generation step including (a) a decomposition step of generating a decomposed product of the 3-hydroxycarboxylic acid polymer, and (b) a dehydration step of generating (meth)acrylic acid by bringing the decomposed product into contact with a dehydration catalyst.

The present invention also relates to a method for producing a hydrophilic resin, including polymerization of a monomeric component containing (meth)acrylic acid obtained by any of the methods for producing (meth)acrylic acid according to the first to third aspects of the present invention.

The present invention also relates to the method for producing (meth)acrylic acid or the method for producing a hydrophilic resin, further including a fermentation step, wherein through the fermentation step, the 3-hydroxycarboxylic acid used as the starting material is generated.

The present invention also relates to the method for producing (meth)acrylic acid or the method for producing a hydrophilic resin, wherein the 3-hydroxycarboxylic acid is 3-hydroxypropionic acid.

The present invention also relates to the method for producing (meth)acrylic acid or the method for producing a hydrophilic resin, wherein trimer to eicosamer in the 3-hydroxycarboxylic acid polymer constitute 10% by mass or more of a total of 100% by mass of the 3-hydroxycarboxylic acid and the 3-hydroxycarboxylic acid polymer, and the (meth)acrylic acid generation step includes heating the composition to generate (meth)acrylic acid.

The present invention also relates to the method for producing (meth)acrylic acid or the method for producing a hydrophilic resin, wherein the (meth)acrylic acid generation step includes (a) a decomposition step of generating a decomposed product of the 3-hydroxycarboxylic acid polymer, and (b) a dehydration step of generating (meth)acrylic acid by bringing the decomposed product into contact with a dehydration catalyst.

The present invention also relates to the method for producing (meth)acrylic acid or the method for producing a hydrophilic resin, wherein the decomposition step is performed by heating.

The present invention also relates to the method for producing a hydrophilic resin, wherein the hydrophilic resin is a water-absorbing resin.

The present invention also relates to a resin composition containing a hydrophilic resin obtainable by the production method of the present invention, the composition containing a nitrogen-containing compound that gives an amount of nitrogen of 80 ppm by mass or less based on the hydrophilic resin.

That is, the first aspect of the present invention reduces variation of the material composition to enable stable plant operation. Also, the preliminary oligomerization (esterification) decreases the hydroxy group concentration in the starting material to reduce the load in the dehydration reaction, so as to enhance the productivity of acrylic acid.

The second aspect of the present invention, in other words, has been made in view of the problems that in a 3-hydroxycarboxylic acid polymer contained in a material composition, the amount of water contained in the polymer is naturally large and the cost for evaporation is large if the polymer contains a large amount of low molecular components, while the material composition forms a suspension solution which tends to cause clogging or a decrease in the yield of acrylic acid if the polymer contains a large amount of high molecular weight components. The second aspect of the present invention employs the material composition containing 10% by mass or more (in the range falling between the above amounts) of trimer to eicosamer, and therefore gives utility which is not so high and a yield of acrylic acid which is high.

The third aspect of the present invention, in other words, can suppress clogging or activity reduction by depolymerizing oligomers before dehydration in the decomposition step.

Advantageous Effects of Invention

The present invention can provide a method for producing (meth)acrylic acid which can stably produce (meth)acrylic acid with high productivity. The present invention can also suitably produce a hydrophilic resin using (meth)acrylic acid produced by the present method. Furthermore, the present invention can provide a composition that contains a reduced amount of a nitrogen-containing compound and contains (meth)acrylic acid or a hydrophilic resin.

DESCRIPTION OF EMBODIMENTS

Figure 1:
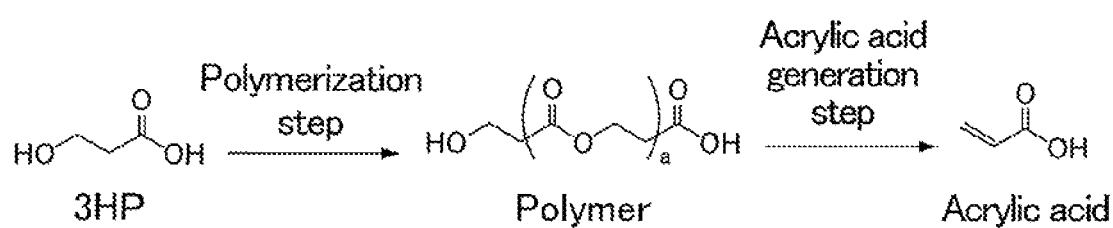
FIG. 1 is a view illustrating a reaction formula with 3HP as a starting material according to the production method of a first aspect of the present invention.

Hereinafter, the present invention is described in detail.

Here, any combination of at least two of the following preferred features of the present invention is also a preferred embodiment of the present invention.

Hereinafter, the methods for producing (meth)acrylic acid according to the first to third aspects of the present invention are described in order. The methods for producing (meth)acrylic acid according to the first to third aspects of the present invention can suitably employ the other features of the present invention.

(Method for Producing (Meth)Acrylic Acid According to the First Aspect of the Present Invention)

The first aspect of the present invention can provide a method for producing (meth)acrylic acid which enhances the productivity or reduces the amount of the catalyst, and enables stable production of (meth)acrylic acid at low cost. With the (meth)acrylic acid obtained by the present method, a hydrophilic resin can be suitably produced. A composition containing a 3-hydroxycarboxylic acid polymer herein is also referred to as a material composition containing a 3-hydroxycarboxylic acid polymer or simply as a material composition.

Examples of the 3-hydroxycarboxylic acid of the first aspect of the present invention include 3HP and 3-hydroxyisobutyric acid. Preferred among these is 3HP. Examples of the (meth)acrylic acid include acrylic acid and methacrylic acid. Preferred among these is acrylic acid.

The above 3-hydroxycarboxylic acid species can be used alone or in combination. Also, the (meth)acrylic acid obtained is different depending on the kind of the 3-hydroxycarboxylic acid used.

The polymerization step of polymerizing the 3-hydroxycarboxylic acid to generate a composition containing a 3-hydroxycarboxylic acid polymer is preferably a purification and condensation step for 3-hydroxycarboxylic acid. The step is preferably a step of purifying and condensing fermented mash of 3-hydroxycarboxylic acid, for example. The purification and condensation of the purification and condensation step can be and may be performed separately or simultaneously depending on the operation.

It is also possible to allow the polymerization to proceed while storing 3-hydroxycarboxylic acid obtained in the purification and condensation step under predetermined conditions.

That is, an example of a preferred method suitably applicable to the method for producing (meth)acrylic acid according to the first aspect of the present invention includes, in the following order, the fermentation step of generating 3-hydroxycarboxylic acid as a starting material, the purification and condensation step of allowing oligomerization of the 3-hydroxycarboxylic acid to proceed, and the step of generating (meth)acrylic acid from a composition containing a 3-hydroxycarboxylic acid polymer obtained in the purification and condensation step. The above step of generating (meth)acrylic acid from a composition containing a 3-hydroxycarboxylic acid polymer is a step of obtaining (meth) acrylic acid by further decomposing and dehydrating compounds such as oligomers obtained in the above purification and condensation step. Through such a step, it is possible to reduce the load in the whole dehydration reaction to enhance the productivity or reduce the amount of the catalyst compared to the case of performing a one-stage dehydration reaction because the dehydration reaction can be performed in multiple stages differently from the case of obtaining (meth)acrylic acid through a one-stage dehydration reaction using 3-hydroxycarboxylic acid.

The purification and condensation step in the above polymerization step is preferably performed by a step including at least one operation selected from the group consisting of membrane separation, distillation and evaporation, electrodialysis, and extraction, for a solution of 3-hydroxycarboxylic acid, for example. Here, the step preferably includes a step performed at 40° C. or higher, more preferably at 50° C. or higher, and still more preferably at 60° C. or higher. With such a step, the oligomerization proceeds more rapidly. The specific contents of the operations are described later as the "methods for obtaining a material composition with a small amount of impurities".

The material composition containing a 3-hydroxycarboxylic acid polymer may be any material composition containing a 3-hydroxycarboxylic acid polymer. The material composition may also contain a monomer of 3-hydroxycarboxylic acid, a solvent, a byproduct generated in preparation of the 3-hydroxycarboxylic acid, or the like substance.

The material composition containing a 3-hydroxycarboxylic acid polymer used in the present invention contains 3-hydroxycarboxylic acid polymer including trimer or higher order units (units with "a" in the later-described formula (1) being 2 or higher) of the polymer which constitute 3% by mass or more of a total of 100% by mass of the 3-hydroxycarboxylic acid and the polymer thereof. The trimer or higher order units preferably constitute 5% by mass or more from the viewpoint of improving the properties such as the yield of the (meth)acrylic acid, more preferably 7% by mass or more, still more preferably 10% by mass or more, further more preferably 15% by mass or more, particularly preferably 20% by mass or more, and most preferably 25% by mass or more. From the viewpoint of the cost and equipment required for preparation of a material composition, the concentration is preferably 95% by mass or less, and more preferably 90% by mass or less.

The concentration of the 3-hydroxycarboxylic acid and a polymer thereof in the material composition containing the 3-hydroxycarboxylic acid polymer together is preferably 10% by mass or more based on 100% by mass of the composition, more preferably 15% by mass or more, still more preferably 20% by mass or more, even more preferably 30% by mass or more, and particularly preferably 40% by mass or more. The concentration is preferably 95% by mass or less, more preferably 93% by mass or less, and still more preferably 90% by mass or less.

If the concentration of the solute is increased (for example, to 15% by mass or higher) and the concentration of water is decreased, the cost for heating and evaporation in steps such as the step of generating (meth)acrylic acid can also be reduced. In contrast, if the concentration is set to 95% by mass or lower, excessive heating and equipment required for an increase in the concentration is not necessary, which is advantageous in terms of the cost.

The concentration of the 3-hydroxycarboxylic acid polymer contained in the material composition is preferably 10 to 95% by mass, more preferably 15 to 93% by mass, still more preferably 20 to 90% by mass, particularly preferably 30 to 90% by mass, and most preferably 40 to 90% by mass.

The 3-hydroxycarboxylic acid polymer herein refers to a polymer in which 3-hydroxycarboxylic acid molecules are linked by intermolecular ester bonds.

Examples of the 3-hydroxycarboxylic acid polymer include, for example in the case of a 3HP polymer, polyesters in which a hydroxy group and a carboxyl group in 3HP are linked by an intermolecular ester bond as illustrated in the following formula (1).

In the formula, "a" can be any value, but in the present invention, if a polymer having a value of "a" in a specific range is contained in the material composition in a specific concentration, the productivity is increased or the amount of the catalyst is reduced, and (meth)acrylic acid can be stably produced at low cost.

[Chem. 1]

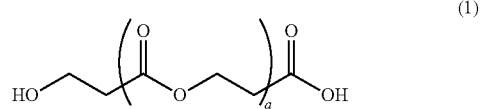

(1)

3-Hydroxycarboxylic acid molecules are likely to form an oligomer or a polymer linked by ester bonds through an intermolecular dehydration reaction. This reaction may proceed very easily depending on the conditions such as the concentration, the temperature, and the coexisting compounds, and an oligomer is generated even during storage at room temperature, eventually forming an equilibrium composition. If the 3-hydroxycarboxylic acid molecules are further heated in steps such as the purification and condensation step for fermented mash, oligomers are generated at a higher speed. Since the oligomerization reaction is an equilibrium reaction in which water is produced as a byproduct, the equilibrium composition depends on the concentration of water. The amount of low molecular oligomers is large if the concentration of water is high, while the amount of high molecular weight oligomers is large if the concentration of water is low.

A high molecular weight 3-hydroxycarboxylic acid polymer can be prepared by a reaction with removal of water from the 3-hydroxycarboxylic acid. For example, such a polymer can be obtained by forming an oligomer by heating, and further reacting the oligomer while removing water under reduced pressure in the presence of a catalyst. Also in this case, the average molecular weight and the amount of trimer or higher order units change depending on the water removal level. It is also possible to form a 3-hydroxycarboxylic acid polymer having a high molecular weight in a microorganism.

From the viewpoint of increasing the yield of (meth) acrylic acid, the material composition containing a 3-hydroxycarboxylic acid polymer preferably contains a 3-hydroxycarboxylic acid polymer including trimer (a=2 in the formula (1)) to nonamer (a=8 in the formula (1)) units which constitute 3% by mass or more of a total of 100% by mass of the 3-hydroxycarboxylic acid and the 3-hydroxycarboxylic acid polymer. The amount of these units is more preferably 5% by mass or more, still more preferably 10% by mass or more, even more preferably 15% by mass or more, further more preferably 20% by mass or more, particularly preferably 30% by mass or more, and most preferably 40% by mass or more. From the viewpoint of the cost and equipment required for preparation of a material composition, the amount of the units is preferably 95% by mass or less, and more preferably 90% by mass or less.

The 3-hydroxycarboxylic acid components and low molecular components such as about dimer to nonamer units can be analyzed by liquid chromatography, and components such as decamer or higher order units can be analyzed by size exclusion chromatography.

The 3-hydroxycarboxylic acid units contained in the material composition can be determined from the analytical value of liquid chromatography or size exclusion chromatography. Alternatively, the 3-hydroxycarboxylic acid units can be determined by heating the material composition containing the 3-hydroxycarboxylic acid polymer in an alkaline aqueous solution (e.g. sodium hydroxide aqueous solution), hydrolyzing the composition, and quantifying the generated 3-hydroxycarboxylic acid by liquid chromatography.

Here, a 3-hydroxycarboxylic acid unit refers to —$CH_2$—CHR—COO— (R is hydrogen or a methyl group). The 3-hydroxycarboxylic acid molecules are counted in the following manner: 1 mol of 3-hydroxycarboxylic acid is counted as 1 mol of 3-hydroxycarboxylic acid units, 1 mol of 3-hydroxycarboxylic acid dimer units is counted as 2 mol of 3-hydroxycarboxylic acid units, 1 mol of 3-hydroxycarboxylic acid trimer units is counted as 3 mol of 3-hydroxycarboxylic acid units, and so forth.

In the present invention, (meth)acrylic acid is generated by reacting such a 3-hydroxycarboxylic acid polymer by a method such as heating or bringing the polymer into contact with a catalyst. In the reaction, ester groups of the polymer are decomposed to form 3-hydroxycarboxylic acid, a 3-hydroxycarboxylic acid polymer with a decreased degree of polymerization, acrylic acid, and an acrylic acid polymer, or the hydroxy groups of the 3-hydroxycarboxylic acid or the 3-hydroxycarboxylic acid polymer are dehydrated to generate acrylic acid and an acrylic acid polymer. Allowing these reactions to proceed in combination enables effective generation of (meth)acrylic acid.

In the method for producing (meth)acrylic acid of the first aspect of the present invention, use of the above specific material composition enhances the productivity or reduces the amount of a catalyst, and also enables stable production of (meth)acrylic acid at low cost.

The material composition containing a 3-hydroxycarboxylic acid polymer is preferably heated in the step of generating (meth)acrylic acid. Hereinafter, the material composition containing a 3-hydroxycarboxylic acid polymer and the heating (decomposition and/or dehydration) of the material composition are described in the stated order.

The material composition containing a 3-hydroxycarboxylic acid polymer may contain a solvent. The solvent is not particularly limited if it can dissolve 3-hydroxycarboxylic acid and polymers thereof. Examples of the solvent include water, alcohols, hydrocarbons, ethers, ketones, esters, amines, and amides. These may be used alone or in combination. The solvent preferably has a lower boiling point than the 3-hydroxycarboxylic acid for smoother evaporation. For example, water is preferred.

In the first aspect of the present invention, if the material composition contains a solvent, the concentration of the solvent in 100% by mass of the material composition is preferably 5 to 90% by mass, more preferably 7 to 85% by mass, still more preferably 10 to 80% by mass, particularly preferably 10 to 70% by mass, and most preferably 10 to 60% by mass. If the concentration of the solvent is 5% by mass or higher, the viscosity of the material composition decreases to allow easier handling of the material composition and, in the case that the step of generating (meth)acrylic acid is accompanied by evaporation of the material composition or the generated product, the effect of promoting evaporation of 3-hydroxycarboxylic acid, polymers thereof, acrylic acid, and polymers thereof is expected. If the concentration is 90% by mass or lower, the amount of heat required for the heating and evaporation can be suppressed, which contributes to reduction in the utilities cost.

If the material composition contains water, the concentration of water is preferably adjusted appropriately because, as described above, water has influence on the composition distribution of the 3-hydroxycarboxylic acid polymer. The concentration of water contained in the material composition containing the 3-hydroxycarboxylic acid polymer is preferably from 5% by mass to 90% by mass inclusive in 100% by mass of the composition.

Also, the present invention relates to a method for producing (meth)acrylic acid using 3-hydroxycarboxylic acid as a starting material, and the method includes the polymerization step of polymerizing the 3-hydroxycarboxylic acid to generate a composition containing a 3-hydroxycarboxylic acid polymer, and the step of generating (meth)acrylic acid from the composition including a 3-hydroxycarboxylic acid polymer, wherein the concentration of water contained in the material composition obtained in the above polymerization step is preferably from 5% by mass to 90% by mass inclusive based on 100% by mass of the composition.

The concentration of water is more preferably 7% by mass or higher, and still more preferably 10% by mass or higher. The concentration is more preferably 85% by mass or lower, still more preferably 80% by mass or lower, further more preferably 70% by mass or lower, and particularly preferably 60% by mass or lower.

The material composition containing a 3-hydroxycarboxylic acid polymer may also contain components such as by-products generated by the synthesis of the 3-hydroxycarboxylic acid by fermentation or the like method, as well as the 3-hydroxycarboxylic acid and polymers thereof. Specific examples of the by-products include components that can be generated together with 3-hydroxycarboxylic acid by fermentation, such as formic acid, acetic acid, propionic acid, butyric acid, succinic acid, fumaric acid, pyruvic acid, glycolic acid, lactic acid, ethanol, amino acids, 1,3-propanediol, glycerol, hydroxypropionaldehyde, and alanine.

The 3-hydroxycarboxylic acid used in the present invention can be obtained from various resources, but is preferably obtained from a bioresource that can be recycled as a carbon source, from the viewpoint of suppression of global warming and environmental protection. More specifically, 3-hydroxycarboxylic acid may be prepared by fermentation of saccharides obtained from agricultural products or saccharides obtained by degrading cellulose, for example.

In the present invention, at least part or all of the 3-hydroxycarboxylic acid species contained in the material composition is preferably 3-hydroxycarboxylic acid species obtained by fermentation.

Also, the 3-hydroxycarboxylic acid is preferably formed from a bioresource such as biomass.

3-Hydroxycarboxylic acid is also obtainable by a known method, such as the fermentation using *Escherichia coli* containing a beta-alanine aminotransferase derived from the strain *Streptomyces griseus* ATCC 21897 with glucose as a carbon source, which is described in WO 2008/027742. Also, 3-hydroxycarboxylic acid can be obtained by fermentation with glycerol as a carbon source, using glycerol dehydratase derived from *Klebsiella pneumoniae* and *Escherichia coli* that contains *Escherichia coli*-derived aldehyde oxidase which is described in WO2001/016346.

The above publications are examples of the method for obtaining 3-hydroxycarboxylic acid, but bacteria or genetically modified bacteria used for fermentation is not particularly limited, and any 3-hydroxycarboxylic acid species obtained by fermentation using an organism capable of generating 3-hydroxycarboxylic acid is usable in the present method. Other than 3-hydroxycarboxylic acid obtained by fermentation, 3-hydroxycarboxylic acid generated by bringing a saccharide as the starting material and an organism into contact with each other can also be converted into (meth)acrylic acid by the present method.

The material composition containing a 3-hydroxycarboxylic acid polymer used in the present invention is preferably a material composition that is obtained through the fermentation step and has a smaller amount of impurities. Examples of the impurities in the material composition obtained through the fermentation step include bacterial cells, protein, amino acids, glucose, salts, and fermentation by-products described above which are typically contained in a fermented mash.

Examples of the method for obtaining a material composition with a small amount of impurities include a method of preparing a material composition using 3-hydroxycarboxylic acid obtained through the purification step from the fermented mash. The purification step from fermented mash can be a known method. Specific examples of the method include a method of purifying 3-hydroxycarboxylic acid by precipitating crude 3-hydroxycarboxylic acid obtained by fermentation using a calcium salt, collecting the calcium salt of 3-hydroxycarboxylic acid, and reacting the salt with an acid such as sulfuric acid; and a method of purifying 3-hydroxycarboxylic acid by chemically converting ammonium-type 3-hydroxycarboxylic acid obtained by fermentation into 3-hydroxycarboxylic acid by electrodialysis or the cation exchange method.

Furthermore, a method utilizing a membrane-separation operation can be used, such as removal of the impurities using typically used filter, an MF membrane (microfiltration membrane), or an UF membrane (ultrafiltration membrane), or condensation of the 3-hydroxycarboxylic acid using an RO membrane (reverse osmosis membrane).

Also, an amine solution of 3-hydroxycarboxylic acid can be obtained through extraction by adding a water-immiscible amine solvent to an aqueous solution of 3-hydroxycarboxylic acid or an ammonium salt thereof obtained by fermentation, and heating the mixture according to need. The amine solution is then back extracted with water under heat, so that an aqueous solution of 3-hydroxycarboxylic acid is obtained.

It is also possible to perform purification by evaporation or distillation using the vapor pressure of the 3-hydroxycarboxylic acid. However, since the vapor pressure of 3-hydroxycarboxylic acid is small, an operation under a highly reduced pressure is preferred.

Also, purified 3-hydroxycarboxylic acid can be obtained by esterifying 3-hydroxycarboxylic acid with an alcohol, purifying and condensing the obtained 3-hydroxycarboxylic acid ester through distillation, and hydrolyzing the 3-hydroxycarboxylic acid ester.

Furthermore, water can be removed, and 3-hydroxycarboxylic acid can be condensed by an evaporation or distillation operation from an aqueous solution of 3-hydroxycarboxylic acid. For example, a method using a multiple effect evaporator is a suitable example.

Performing the above operations alone or in combination in the polymerization step for 3-hydroxycarboxylic acid enables production of a material composition containing a 3-hydroxycarboxylic acid polymer while purifying and condensing the 3-hydroxycarboxylic acid.

If 3-hydroxycarboxylic acid is produced by fermentation, the fermented mash in many cases also contains a nitrogen-containing compound such as protein and amino acids derived from a microorganism (e.g. bacterial cells), ammonia used for pH adjustment of the fermented mash, and an amine as a solvent used in the case of performing an extraction operation on the fermented mash. In the case of producing a material composition containing a 3-hydroxycarboxylic acid polymer by a method as described above, the conditions for the purification and condensation step are preferably set such that the amount of nitrogen contained in the material composition is 0.2% by mass or less based on a total of 100% by mass of the 3-hydroxycarboxylic acid and the 3-hydroxycarboxylic acid polymer. The amount is more preferably 0.1% by mass or less, still more preferably 0.05% by mass or less, and further more preferably 0.01% by mass or less. If the amount is more than 0.2% by mass, a nitrogen-containing compound may be produced as a by-product in the later step of producing (meth)acrylic acid. Examples of the nitrogen-containing compound include (meth)acrylamides, cyclic nitrogen compounds having a pyridine ring or a pyrrole ring, lactams such as pyrrolidone, and amines. Here, particularly harmful (meth)acrylamides may be generated, which may require another step for removal of the harmful (meth)acrylamides, or may limit the use range of the (meth)acrylic acid. Examples of the (meth)acrylamides include acrylamide, N-methylacrylamide, methacrylamide, and N-methylmethacrylamide. Use of a material composition containing nitrogen in the above range can give a total amount of nitrogen in the nitrogen-containing compound of 80 ppm or less based on the generated (meth)acrylic acid. The total amount is preferably 60 ppm by mass or less, and more preferably 50 ppm by mass or less. Similarly, a composition with 10 ppm by mass or less of the (meth)acrylamides based on the (meth)acrylic acid can be obtained. The amount of the (meth)acrylamides is preferably 5 ppm by mass or less, and more preferably 1 ppm by mass or less. Also, as described later, purification of the composition can produce (meth)acrylic acid with 10 ppm by mass or less of (meth)acrylamides based on the (meth)acrylic acid.

If the total amount of nitrogen in the nitrogen-containing compound is 80 ppm by mass or less based on the mass of the (meth)acrylic acid, generation of irritating odor from the (meth)acrylic acid can be suppressed. Also, if the amount of the (meth)acrylamides is 10 ppm by mass or less, the resulting (meth)acrylic acid is non-toxic and non-irritating. The "total amount of nitrogen" is the total amount of nitrogen included in elements constituting the nitrogen-containing compound. The total amount of nitrogen in the nitrogen-containing compound contained in the composition can be analyzed in accordance with the Japanese Industrial Standard K0102 or K2609. Also, the (meth)acrylamides can be analyzed by gas chromatography or liquid chromatography.

Production of (meth)acrylic acid directly from 3-hydroxycarboxylic acid through the dehydration reaction is known, but as described above, 3-hydroxycarboxylic acid is easily oligomerized (polymerized). Hence, if the acid is to be used as a monomer, the acid is required to be in a highly diluted solution. In this case, the load in the reaction, such as an increase in the size of the reactor and an increase in the amount of heat required for the heating. Also, in the case that the reaction involves evaporation as in the case of a vapor phase reaction, the amount of heat required is enormous.

Meanwhile, the dehydration reaction (intramolecular dehydration) of 3-hydroxycarboxylic acid commonly requires high-temperature conditions, and is known to cause a decrease in the catalytic activity even if a catalyst is used. Polymerization of 3-hydroxycarboxylic acid is different in the reaction mechanism, but is a kind of dehydration reaction (intermolecular dehydration), and is the same in terms of decreasing the hydroxy groups of the 3-hydroxycarboxylic acid. This reaction occurs at relatively low temperatures, and easily proceeds even at room temperature or even without a catalyst, if the concentration of the 3-hydroxycarboxylic acid is high. In order to obtain (meth)acrylic acid from the generated polymer, the polymer needs to be further decomposed. In the case of obtaining (meth)acrylic acid from 3-hydroxycarboxylic acid, a dehydration reaction is required.

In the first aspect of the present invention, if the hydroxy groups of the 3-hydroxycarboxylic acid is reduced by allowing the dehydration reaction to proceed through a polymerization reaction (oligomerization reaction) under moderate conditions, (meth)acrylic acid can be easily generated in the subsequent (meth)acrylic acid generation step. Even in the case of generating (meth)acrylic acid by intramolecular dehydration reaction of the residual hydroxy groups in the (meth)acrylic acid generation step, reduction of the hydroxy groups by the polymerization reaction (oligomerization reaction) performed in advance decreases the load in the intramolecular dehydration requiring severe conditions, generating (meth)acrylic acid more efficiently.

Next, the method for producing (meth)acrylic acid from a material composition containing a 3-hydroxycarboxylic acid polymer is described.

The method can be performed by heating, for example. The heating step can be performed in the presence or absence of a catalyst.

If the heating step is performed in the absence of a catalyst, the heating temperature is preferably 180° C. to 700° C., more preferably 190° C. to 650° C., and still more preferably 200° C. to 600° C. If the temperature is lower than 180° C., the heating may be insufficient to decrease the yield of the (meth)acrylic acid or cause unreacted polymer to be accumulated in the heater, causing clogging in the heater or a decrease in the heating efficiency due to a decrease in the thermal conductivity. If the temperature is higher than 700° C., the amount of by-products produced by heating is large, which may cause a decrease in the yield of the (meth)acrylic acid, a decrease in the purity of the obtained (meth)acrylic acid, or complication of the (meth)acrylic acid purification step.

If the heating step is performed in the presence of a catalyst, the heating temperature is preferably 150° C. to 600° C., more preferably 160° C. to 550° C., still more preferably 170° C. to 500° C., and particularly preferably 180° C. to 450° C.

Examples of the catalyst used in the heating step include, but not particularly limited to, acid catalysts and base catalysts. In particular, solid acid catalysts and solid basic catalyst are preferred.

In the case that the material composition or the product is to be evaporated, a low pressure in the heater is favorable because evaporation is likely to be caused as the pressure decreases. Still, the pressure should be selected in consideration of easiness in collecting the product and the cost for the equipment and other conditions. The pressure in the heater is preferably 10 kPa to 1000 kPa, more preferably 30 kPa to 300 kPa, and still more preferably 50 kPa to 250 kPa.

The heater preferably has a structure that efficiently conducts heat to the material composition supplied in the form of a liquid. Examples of the heater include horizontal-tube or vertical-tube natural circulation heaters, forced-circulation heaters, and multi-tubular heat exchangers.

Here, it is also possible to perform the reaction by filling the channels for the material composition in the heater with packing having a large surface area per unit filling volume, including irregular packing and regular packing such as a Raschig ring, a Berl saddle, a spherical molded product, or a wire gauze molded product (e.g. Dixon packing, McMahon packing), and Mellapak (from Sulzer Chemtech Ltd.), and supplying the material composition to the channels such that the surface area coming into contact with the material composition (liquid) increases. Thereby, the material composition supplied comes into contact with packing having a large surface area, which increases the heat transfer area to enable efficient heat transfer and allow the reaction to proceed in a short time. Accordingly, the side reaction in the heater can be suppressed.

Examples of the material of the packing include metal materials such as iron and stainless steel, and inorganic materials such as silica and ceramic.

The material composition may be heated in a fluidized bed heater. For example, the material composition may be reacted by fluidizing an inert solid in the powder form with inert gas, and supplying the material composition to the heated fluidized bed heater.

Also, another preferred embodiment is a method of holding a certain amount of a liquid phase in a heater, causing a reaction of generating (meth)acrylic acid in the liquid phase while supplying the material composition in the liquid form, and then evaporating the generated (meth)acrylates to remove them from the heater. The residence time required for generation of (meth)acrylic acid is controllable by the temperature, the pressure, the amount of heat, and the amount of the liquid materials in the heater. In order to suppress distillation of the 3-hydroxycarboxylic acid, a 3-hydroxycarboxylic acid polymer with a low degree of polymerization, and a (meth)acrylic acid polymer, the heater may be provided with a distillation column to provide reflux.

Also, in order to facilitate evaporation of the product generated by heating, a heating step may be performed in the presence of an inert gas. Examples of the inert gas include water vapor, nitrogen, helium, argon, and carbon dioxide. Preferred among these are water vapor and nitrogen.

The amount of supply of the inert gas is preferably 0.5 to 100, more preferably 1 to 50, times the number of moles of the 3-hydroxycarboxylic acid units contained in the material composition. If the material composition contains water, vapor generated by evaporation of the water in the heating step is also included in the inert gas.

Heating the material composition under the above conditions depolymerizes (decomposes) the 3-hydroxycarboxylic acid polymer through the reactions, efficiently generating (meth)acrylic acid. Dehydration of the 3-hydroxycarboxylic acid contained in the material composition or the 3-hydroxycarboxylic acid generated upon decomposition of the polymer further generates (meth) acrylic acid.

The (meth)acrylic acid generation step may be performed in the presence of a polymerization inhibitor to suppress radical polymerization where the generated double bonds of (meth)acrylic acid and the polymers thereof are polymerized. Examples of the polymerization inhibitor include methoquinone, manganese acetate, nitrosophenol, cupferron, N-oxyl compounds, copper dibutylthiocarbamate, phenothiazine, and hydroquinone. Also, according to need, oxygen-containing gas may be supplied.

The heating step may be the step of bringing the material composition into contact with a catalyst, or may be multi-stage heating step of performing the above heating step, and then further bringing the generated product into contact with a dehydration catalyst. Thereby, the yield of (meth)acrylic acid can be further increased. Particularly in the case of the multi-stage heating step, the polymerization step is performed in advance as in the present invention to generate a material composition containing a 3-hydroxycarboxylic acid polymer, and thus the load in the step of bringing the composition into contact with a dehydration catalyst (dehydration step) can be reduced, so that the productivity of the (meth)acrylic acid can be enhanced or the amount of the catalyst can be reduced.

The reactor to be used in the dehydration step of bringing the composition into contact with a dehydration catalyst may be any reactor capable of holding a solid catalyst therein and heating the catalyst, such as a fixed-bed continuous reactor or a fluid-bed continuous reactor. Preferred is a fixed-bed continuous reactor.

The dehydration step is preferably a vapor phase reaction in which the outlet gas obtained from the first stage of the heating step is brought into contact with a dehydration catalyst. If the step is a vapor phase reaction, deposition of heavy components on the dehydration catalyst and activity deterioration accompanied by the deposition can be suppressed, and clogging of the reaction tubes can also be suppressed.

In the case of using a fixed-bed continuous reactor, the reactor filled with a catalyst may be heated, and then vapor of the material composition may be supplied to the reactor. The vapor of the material composition can suitably be any of upflow, downflow, and horizontal flow. In terms of easiness of heat exchange, a fixed-bed multi-tubular continuous reactor can be suitably used.

In the case of using a fluid-bed continuous reactor, a catalyst in a powder form is charged in the reactor, and the reaction can be caused while the catalyst is flown by the vapor of the material composition, inert gas separately supplied to the reactor, or the like. Since the catalyst is flowing, clogging due to the heavy components is not likely to occur. It is also possible to continuously extract part of the catalyst to continuously supply a new catalyst or recycled catalyst.

The dehydration catalyst is not particularly limited if the catalyst is capable of catalysis which converts 3-hydroxycarboxylic acid to (meth)acrylic acid.

Examples of the dehydration catalyst include crystalline metallosilicate such as zeolite; compounds obtained by loading a metal such as an alkali metal, an alkaline earth metal, or a transition metal onto a crystalline metallosilicate by a method such as ion exchange; natural or synthetic clay compounds such as kaolinite, bentonite, and montmorillonite; catalysts obtained by loading sulfuric acid, heteropolyacid, phosphoric acid or phosphate (alkali metal salt of phosphoric acid, alkaline earth metal salt, manganese phosphate, zirconium phosphate), an alkali metal, or an alkaline earth metal onto a carrier such as alumina or silica; inorganic oxides or inorganic composite oxides, such as $Al_2O_3$, $SiO_2$, $TiO_2$, $ZrO_2$, $SnO_2$, $V_2O_5$, $SiO_2$—$Al_2O_3$, $SiO_2$—$TiO_2$, $SiO_2$—$ZrO_2$, $TiO_2$—$WO_3$, and $TiO_2$—$ZrO_2$; solid acid substances such as sulfates or phosphates of a metal such as $MgSO_4$, $Al_2(SO_4)_3$, $K_2SO_4$, $AlPO_4$, or $Zr(SO_4)_2$; and solid basic substances such as calcium oxide, magnesium oxide, and hydrotalcite. Preferred among these are $Al_2O_3$, $SiO_2$, $SiO_2$—$Al_2O_3$, $TiO_2$, zeolite, zeolite on which an alkali metal or an alkaline earth metal is supported, catalysts obtained by loading phosphoric acid, phosphate, an alkali metal, or an alkaline earth metal onto a carrier such as silica.

The dehydration catalyst may be a catalyst molded body. Examples of the shape of the molded body include, but not limited to, a spherical shape, a cylindrical shape, a ring shape, and a honeycomb shape.

Regarding the physical properties of the above dehydration catalyst, from the viewpoints of the catalytic activity, the specific surface area determined by the BET method is preferably 0.01 to 500 $m^2$/g, and more preferably 0.1 to 400 $m^2$/g. From the viewpoints of the catalytic activity, the (meth)acrylic acid selectivity of the product, and the catalyst life, the Hammett acidity function $H_0$ is preferably +4 to −10, more preferably +2 to −9. From the viewpoints of the catalytic activity and the pressure loss of the reactor, the size of the dehydration catalyst in major axis is preferably 0.1 mm to 50 mm, and more preferably 0.5 mm to 40 mm.

The temperature of the catalyst layer is preferably held at 150° C. to 500° C., more preferably 200° C. to 450° C., still more preferably 220° C. to 430° C., and further more preferably 250° C. to 400° C. If the temperature is in the above range (150° C. to 500° C.), the reaction speed is high, and a by-product is not likely to be produced, so that the yield of the (meth)acrylic acid is high.

The reaction pressure is not particularly limited, but can be determined in consideration of the productivity in the dehydration reaction, the collection efficiency after the dehydration reaction, and the like conditions. The reaction pressure is preferably 10 kPa to 1000 kPa, more preferably 30 kPa to 300 kPa, and still more preferably 50 kPa to 250 kPa.

As described above, the multi-stage heating step, which is a combination of the heating step and the step of bringing the composition into contact with a dehydration catalyst, generates (meth)acrylic acid through decomposition of a 3-hydroxycarboxylic acid polymer, and the resulting product and the dehydration catalyst are brought into contact with each other. Thereby, the 3-hydroxycarboxylic acid contained in the material composition and the 3-hydroxycarboxylic acid generated by decomposition of the polymer are dehydrated, and also the (meth)acrylic acid can be produced efficiently with an increased yield.

Also, depolymerizing the polymer in the heating step as described above produces decomposed products having a low degree of polymerization. For example, bringing decomposed products such as dimers, trimers, and tetramers of the (meth)acrylic acid into contact with a dehydration catalyst decomposes these multimers to generate acrylic acid. Alternatively, bringing such decomposed products having a low degree of polymerization, such as dimers, trimers, and tetramers of 3-hydroxycarboxylic acid, into contact with a dehydration catalyst generates 3-hydroxycarboxylic acid and (meth)acrylic acid, and more (meth)acrylic acid units are expected to be generated from the generated 3-hydroxycarboxylic acid by dehydration. Hence, the yield of the (meth)acrylic acid is further increased.

For example, heating can be performed in each of the first heating step (step of decomposing oligomers) and the second heating step (step of performing dehydration in a dehydration reactor), to perform a multi-stage heating step.

The heating step described above enables the reaction of the 3-hydroxycarboxylic acid polymer to be stably maintained, so that (meth)acrylic acid can be efficiently produced.

Performing the dehydration using a dehydration catalyst may cause accumulation of carbonous substances on the catalyst to decrease the catalytic activity. In this case, the catalytic activity can be restored by bringing the carbonous substances into contact with an oxidizing agent (e.g. oxygen), and removing the carbonous substances to regenerate the catalyst. The heating temperature of the catalyst in the catalyst regeneration can shorten the catalyst regeneration time as the temperature increases, but an excessively high temperature may decrease the catalytic activity or the selectivity due to the structural change of the catalyst or the like factors. Typically, the heating temperature is preferably in the range of 300° C. to 800° C., more preferably 320° C. to 700° C., and still more preferably 350° C. to 600° C. If the heating temperature is higher than 800° C., changes may be caused in the physical structures and chemical properties of the catalyst, such as a decrease in the surface area of the catalyst due to sintering or the crystal structure change in the catalyst due to phase change, whereby the catalytic activity and the selectivity may decrease. The upper limit for the temperature is different depending on the kind of the catalyst, but in the case of calcining the catalyst in preparation of the catalyst, the heating is preferably performed at temperatures not higher than the calcining temperature.

In order to control the above heating temperature, the preset conditions such as the preset temperature of the heater for heating the catalyst, the oxidizing agent concentration, and the gas flow amount should be adjusted. In this case, the temperature for heating the catalyst increases as at least one of the preset temperature of the heater and the concentration of the oxidizing agent increases. It is also possible to control the catalyst heating temperature by adjusting at least one of the preset temperature of the heater and the concentration of the oxidizing agent while continuously measuring the catalyst heating temperature. The control method of the catalyst heating temperature described in JP H05-192590 A is also possible.

The oxidizing agent concentration is preferably 1 to 21 vol % from the viewpoints of the temperature control and production cost.

The treatment time is preferably 1 to 100 hours, and more preferably 2 to 50 hours, from the viewpoint of the productivity of the (meth)acrylic acid.

In the present invention, the method for obtaining a composition containing (meth)acrylic acid through cooling of the reaction product obtained at the reactor outlet is not particularly limited. For example, a composition containing (meth)acrylic acid can be obtained by a method of cooling a liquid reaction product using a heat exchanger or introducing a gaseous reaction product into the heat exchanger to condense the reaction product at temperatures not higher than the dew point of the reaction product; or a method of cooling the gaseous reaction product by bringing the gaseous reaction product into contact with an absorbing liquid such as a solvent for absorption.

The (meth)acrylic acid concentration of the composition is preferably 5% by mass or higher, more preferably 10% by mass or higher, and still more preferably 20% by mass or higher. The concentration is also preferably 95% by mass or lower.

The composition of the reaction product obtained thereby contains water and (meth)acrylic acid which are main reaction products, and may also contain by-products, and the solvent and impurities in the material composition. If the solvent is water, the composition may be used in the state of the aqueous solution of (meth)acrylic acid as a starting material for producing a polymer. Addition of a purification step may enable production of (meth)acrylic acid with high purity.

The purification step can be performed by a known technique such as membrane separation, distillation, extraction, and crystallization, and may be performed by these techniques in combination.

The reaction product containing (meth)acrylic acid produced as described above is preferably handled in the collection step and the purification step in the presence of a polymerization inhibitor. Examples of the polymerization inhibitor include methoquinone, manganese acetate, nitrosophenol, cupferron, N-oxyl compounds, copper dibutylthiocarbamate, phenothiazine, and hydroquinone. According to need, oxygen-containing gas may be supplied.

As described above, purification of the composition of (meth)acrylic acid obtained in the present invention enables production of (meth)acrylic acid with high purity. The method of the present invention therefore also provides a method for producing a high-purity (meth)acrylic acid.

The method specifically includes the step of purifying (meth)acrylic acid by crystallization.

The following describes a method for obtaining high-purity (meth)acrylic acid by crystallization of a product obtained by liquefying the above gaseous reaction product by, for example, cold condensation or solvent collection, and removing water and the collection solvent contained in the liquefied product by a known method (e.g. distillation) according to need.

Here, the crude (meth)acrylic acid refers to the composition containing the (meth)acrylic acid obtained in the cooling step, and an aqueous solution of (meth)acrylic acid is particularly suitable.

The crystallization step can be performed by a known method capable of separating propionic acid from the crude (meth)acrylic acid, such as a method described in JP H09-227445 A or JP 2002-519402 T.

After separating (meth)acrylic acid from the product obtained in the (meth)acrylic acid generation step in the purification step described above, for example, the remaining impurities can be reused by recycling. For example, if 3-hydroxycarboxylic acid, a 3-hydroxycarboxylic acid polymer with a low degree of polymerization, or a (meth)acrylic acid polymer is reused as a starting material in the polymerization step or the (meth)acrylic acid generation step, the yield of the (meth)acrylic acid can be increased. The details of the steps are described later.

As described above, in the case of using 3-hydroxycarboxylic acid produced by fermentation, (meth)acrylic acid with greatly reduced amounts of nitrogen and the (meth)acrylamides can be produced by performing the above (meth)acrylic acid generation step and purification step using a material composition containing nitrogen which constitutes 0.2% by mass or less of a total of 100% by mass of the 3-hydroxycarboxylic acid and the polymer thereof. The amount of nitrogen based on the (meth)acrylic acid is preferably 80 ppm by mass or less, more preferably 60 ppm by mass or less, and still more preferably 50 ppm by mass or less. The amount of the (meth)acrylamides based on the (meth)acrylic acid is preferably 10 ppm by mass or less, more preferably 5 ppm by mass or less, and still more preferably 1 ppm by mass or less. Therefore, the present invention relates to a method for producing a composition containing (meth)acrylic acid from 3-hydroxycarboxylic acid obtained by fermentation, and also a method for producing a composition containing (meth)acrylic acid containing 80 ppm or less of nitrogen based on the (meth)acrylic acid. The present invention also relates to a method for producing a composition containing (meth)acrylic acid from 3-hydroxycarboxylic acid obtained by fermentation, and also a method for producing a composition containing (meth)acrylic acid containing 10 ppm or less of (meth)acrylamides based on the (meth)acrylic acid. The present invention also relates to a composition containing (meth)acrylic acid with reduced amounts of nitrogen and (meth)acrylamides as described above.

The present invention also relates to a composition containing (meth)acrylic acid, which contains a nitrogen-containing compound that gives an amount of nitrogen of 80 ppm by mass or less based on the (meth)acrylic acid. The composition of the present invention is preferably obtained by the method for producing (meth)acrylic acid according to the present invention. The method for producing (meth)acrylic acid can appropriately be any of the preferred embodiments described herein. In particular, the method for producing (meth)acrylic acid particularly preferably includes the fermentation step which generates 3-hydroxycarboxylic acid as a starting material. Thereby, it is possible to produce, from a renewable resource, (meth)acrylic acid that is suitable as a starting material for a hydrophilic resin with greatly reduced amounts of nitrogen-containing compounds (e.g. (meth)acrylamides) and nitrogen. This is a notably excellent effect which could not be achieved by the conventional techniques.

With the above method, (meth)acrylic acid can be produced. The (meth)acrylic acid produced thereby is useful as a synthesis material of (meth)acrylic acid derivatives such as (meth)acrylic acid esters, and hydrophilic resins such as poly(meth)acrylic acid and sodium poly(meth)acrylic acid. Therefore, the method for producing (meth)acrylic acid according to the present invention can naturally be combined into the method for producing a (meth)acrylic acid derivative or a hydrophilic resin. The hydrophilic resin is preferably a water-absorbing resin.

The details of the method for producing (meth)acrylic acid according to the first aspect of the present invention described above are the same as the details of the methods for producing (meth)acrylic acid according to the later-described second aspect of the present invention and the third aspect of the present invention, unless otherwise stated.

The effect of stably producing (meth)acrylic acid with high productivity and the effect of suitably producing a hydrophilic resin using the obtained (meth)acrylic acid as described above are the same in the methods for producing (meth)acrylic acid according to the second aspect of the present invention and the third aspect of the present invention. Here, combinations of the concepts of the second aspect of the present invention and the third aspect of the present invention are of course encompassed by the present invention.

Hereinafter, the second aspect of the present invention is described, and then the third aspect of the present invention is described.

(Method for Producing (Meth)Acrylic Acid According to the Second Aspect of the Present Invention)

The method for producing (meth)acrylic acid according to the second aspect of the present invention achieves low cost and suppression of clogging in the reactor or the like instruments and reduction in the catalytic activity, and enables long-term, stable production of (meth)acrylic acid with a high yield.

Specific examples and preferred embodiments of the 3-hydroxycarboxylic acid in the second aspect of the present invention are the same as those described above for the first aspect of the present invention.

The material composition containing a 3-hydroxycarboxylic acid polymer should contain a 3-hydroxycarboxylic acid polymer, and may also contain by-products produced upon synthesis of the 3-hydroxycarboxylic acid by fermentation or the like method. Specific examples of the by-products are the same as those described above for the first aspect of the present invention.

The preferred concentration of the total amount of the 3-hydroxycarboxylic acid and polymers thereof in the material composition and the preferred concentration of the 3-hydroxycarboxylic acid polymer each are the same as that described above for the first aspect of the present invention.

The 3-hydroxycarboxylic acid polymer is the same as that described above, such as the polymer represented by the above formula (1).

The symbol "a" in the formula in the second aspect of the present invention can represent any value. Still, if the material composition of the present invention contains a polymer with a value of "a" falling in a specific range in a specific proportion, the present invention achieves low cost and suppression of clogging in the reactor or the like instruments and a decrease in the catalytic activity, and enables long-term, stable production of (meth)acrylic acid with a high yield.

From the viewpoints such as improvement of the yield of (meth)acrylic acid, the material composition of the second aspect of the present invention contains a 3-hydroxycarboxylic acid polymer, and trimer (a=2 in the formula (1)) to eicosamer (a=19 in the formula (1)) in the 3-hydroxycarboxylic acid polymer constitute 10% by mass or more of a total of 100% by mass of the 3-hydroxycarboxylic acid and a polymer thereof. The amount is preferably 20% by mass or more, more preferably 30% by mass or more, and still more preferably 40% by mass or more. Also, the upper limit for the amount is not particularly limited, but is preferably 95% by mass or less, and more preferably 90% by mass or less from the viewpoints of the cost and equipment required for preparation of the material composition.

From the viewpoint of increasing the yield of the (meth)acrylic acid, the material composition more preferably contains a 3-hydroxycarboxylic acid polymer, and trimer (a=2 in the formula (1)) to pentadecamer (a=14 in the formula (1)) of the 3-hydroxycarboxylic acid polymer constitute 10% by mass or more of a total of 100% by mass of the 3-hydroxycarboxylic acid and a polymer thereof. The amount is more preferably 20% by mass or more, particularly preferably 30% by mass or more, and most preferably 40% by mass or more. The upper limit is not particularly limited, but is preferably 95% by mass or less, and more preferably 90% by mass or less from the viewpoints of the cost and equipment required for preparation of the material composition.

From the viewpoint of increasing the yield of the (meth)acrylic acid, trimer to nonamer (a=8 in the formula (1)) of a 3-hydroxycarboxylic acid polymer in the material composition preferably constitute the same amount as that described above for the first aspect of the present invention, of a total of 100% by mass of the 3-hydroxycarboxylic acid and a polymer thereof.

Also, eicosamer (a=19 in the formula (1)) or higher order units of the 3-hydroxycarboxylic acid polymer in the material composition preferably constitute 50% by mass or less of a total of 100% by mass of the 3-hydroxycarboxylic acid and a polymer thereof. The amount is more preferably 40% by mass or less. If the amount is more than 50% by mass, the viscosity of the material composition may be high to complicate the handling of the composition, or cause deposition of a high molecular weight polymer, causing clogging in the tubes or a decrease or change in the yield of the (meth) acrylic acid due to the various supplied formulations of the material compositions.

The present invention enables production of (meth)acrylic acid by heating such a 3-hydroxycarboxylic acid polymer. The heating promotes the multiple reactions described above for the first aspect of the present invention, thereby effectively generating (meth)acrylic acid.

As described above, a material composition with a large amount of 3-hydroxycarboxylic acid or dimers (i.e. those with a low degree of polymerization) causes industrial problems such as productivity and cost, while a material composition with a large amount of a 3-hydroxycarboxylic acid polymer (i.e. those with a high degree of polymerization) causes problems of handling, clogging, or a decrease in the yield of the (meth)acrylic acid.

Still, the method for producing (meth)acrylic acid according to the second aspect of the present invention, including heating the above specific material composition, can achieve the effect of the second aspect of the present invention described above.

The material composition containing a 3-hydroxycarboxylic acid polymer may contain a solvent. The specific examples and preferred embodiments of the solvent, and the preferred range of the concentration of the solvent such as water are the same as those described for the first aspect of the present invention.

The 3-hydroxycarboxylic acid used in the present invention can be obtained from various sources, but the production method and the other preferred embodiments are the same as those described above for the first aspect of the present invention. As described above, the 3-hydroxycarboxylic acid can be obtained by a known method. Also, a 3-hydroxycarboxylic acid polymer can be produced from a microorganism, and the polymer may be used as the material composition.

The material composition containing a 3-hydroxycarboxylic acid polymer used in the present invention is preferably a material composition that contains a smaller amount of impurities.

The method for obtaining a material composition with a small amount of impurities is the same as that described above for the first aspect of the present invention.

The heating of the material composition containing a 3-hydroxycarboxylic acid polymer (hereinafter, also referred to as a heating step) can be performed in the presence of or the absence of a catalyst.

The preferred heating temperature in the case of performing the heating step in the absence of a catalyst and the preferred heating temperature in the case of performing the heating step in the presence of a catalyst each are the same as that described above for the first aspect of the present invention.

The specific examples and the preferred embodiments of the catalyst used in the heating step are the same as those described above for the first aspect of the present invention.

The preferred range of the pressure in the heater is the same as that described above for the first aspect of the present invention.

The preferred structure, specific examples, and the use method of the heater, and the kind and materials of the packing to be charged into the channels for the material composition each are the same as that described above for the first aspect of the present invention.

In order to facilitate evaporation of the product produced upon heating, the heating step may be performed in the presence of inert gas. The specific examples, preferred embodiments, and preferred amount of supply of the inert gas are the same as those described above for the first aspect of the present invention.

The heating step may be the step of bringing the material composition into contact with a catalyst, or may be a multi-stage heating step of further bringing the product obtained through such a heating step into contact with a dehydration catalyst. Thereby, the yield of the (meth)acrylic acid can be further improved.

The reactor used in the dehydration step of bringing the product into contact with the dehydration catalyst, and the preferred examples and the use method thereof are the same as those described above for the first aspect of the present invention.

The specific examples of the catalyst for the dehydration reaction, i.e., the dehydration catalyst, and the shape of the molded body in the case that the dehydration catalyst is a catalyst molded body, and the other conditions are the same as those described above for the first aspect of the present invention.

The specific surface area determined by the BET method, the Hammett acidity function $H_0$, and the size of the catalyst each are the same as that described above for the first aspect of the present invention.

The preferred range of the temperature of the catalyst layer, and the preferred range of the reaction pressure each are the same as that described above for the first aspect of the present invention.

Such a multi-stage heating step, which is a combination of the heating step and the step of bringing the product into contact with a dehydration catalyst, can achieve the same effect as the effect of the multi-stage heating step described above for the first aspect of the present invention.

The above heating step can stably maintain the reaction of the 3-hydroxycarboxylic acid polymer and can efficiently produce (meth)acrylic acid. Still, the carbonous substances may gradually be adhered to the inside of the heater, the inside of the reactor, and the catalyst. In that case, problems can be caused such as clogging in instruments such as the heater, reactor, and tubes, a decrease in the evaporation efficiency due to a decrease in the heat conductivity of the heater, a decrease in the productivity caused by a decrease in the catalytic activity, and a decrease in the selectivity. In that case, removal of the generated carbonous substances restores the normal conditions.

The catalyst can be recycled by bringing the dehydration catalyst into contact with an oxidizing agent and removing the carbonous substances on the dehydration catalyst.

The oxidizing agent may be a liquid oxidizing agent in which a hydrogen peroxide solution, an organic peroxide, nitric acid, nitrous acid, or the like substance is dissolved, or may be a gaseous oxidizing agent. Preferably, the oxidizing agent is a gaseous oxidizing agent.

A gaseous oxidizing agent is a gas molecule capable of supplying oxygen elements to carbonous substances for oxidative degradation of the carbonous substances. Examples thereof include oxygen (oxygen in the air also corresponds to an oxidizing agent), ozone, nitrogen monoxide, nitrogen dioxide, and nitrous oxide. Any of these oxidizing agents can be used if they contain at least one gaseous oxidizing agent. For example, mixed gases such as a mixed gas of air and oxygen and a mixed gas of nitrogen monoxide and oxygen can be used, and a mixed gas of an oxidizing agent and at least one gas optionally selected from inert gases such as nitrogen, carbon dioxide, argon, helium, and vapor can also be used. Preferred among these is a gas containing oxygen.

The preferred heating temperature for the catalyst in catalyst regeneration is the same as that described above for the first aspect of the present invention.

The method for controlling the heating temperature, the concentration of the oxidizing agent, and the treatment time are the same as those described above for the first aspect of the present invention.

In the present invention, the method for obtaining a composition containing (meth)acrylic acid by cooling the reaction product obtained through the reactor outlet, and the preferred concentration of the (meth)acrylic acid in the composition are the same as those described above for the first aspect of the present invention.

In a composition of the reaction product obtained thereby contains water and (meth)acrylic acid which are the main reaction products, and also may contain by-products, and the solvent and the impurities of the material composition. If the solvent is water, the composition can be used as a starting material for producing a polymer in the state of an aqueous solution of (meth)acrylic acid. Also, addition of the purification step enables production of (meth)acrylic acid with high purity. The specific examples and the preferred embodiments of the purification step are the same as those described above for the first aspect of the present invention.

After separation of the acrylic acid from the product obtained by the process including the heating step, the remaining impurities can be reused by recycling in the same manner as described above for the first aspect of the present invention. The details thereof are described later.

(Method for Producing (Meth)Acrylic Acid According to Third Aspect of the Present Invention)

The method for producing (meth)acrylic acid according to the third aspect of the present invention suppresses clogging in the reactor or the like instruments and a decrease in the catalytic activity, and enables long-term, stable production of the (meth)acrylic acid with a high yield.

Although 3-hydroxycarboxylic acid can be prepared as described above, a 3-hydroxycarboxylic acid polymer is also generated in many cases upon the preparation (for example, in the purification and condensation step of the 3-hydroxycarboxylic acid from fermented mash). The third aspect of the present invention is a method that produces (meth) acrylic acid with a high yield, from a material composition containing not only 3-hydroxycarboxylic acid but also a polymer thereof.

Specific examples and preferred embodiments of 3-hydroxycarboxylic acid according to the third aspect of the present invention are the same as those described above for the first aspect of the present invention.

The material composition containing a 3-hydroxycarboxylic acid polymer may contain substances such as by-products generated upon synthesis of the 3-hydroxycarboxylic acid through a process such as fermentation if it contains the 3-hydroxycarboxylic acid polymer. Specific examples of the by-products are the same as those described above for the first aspect of the present invention.

The preferred concentration of the total amount of the 3-hydroxycarboxylic acid and a polymer thereof and the preferred concentration of the polymer in the material composition each are the same as those described above for the first aspect of the present invention.

The 3-hydroxycarboxylic acid polymer is the same as that described above, such as a polymer represented by the above formula (1).

In the third aspect of the present invention, the symbol "a" in the formula (1) is preferably 1 to 100. From the viewpoints of increasing the yield of acrylic acid and decreasing the decomposed residues, the symbol "a" is preferably 1 to 80, more preferably 2 to 50, and still more preferably 2 to 30.

The material composition used in the present invention contains a 3-hydroxycarboxylic acid polymer. The trimer to eicosamer of the 3-hydroxycarboxylic acid polymer preferably constitute the same amount as that described above for the second aspect of the present invention, of a total of 100% by mass of the 3-hydroxycarboxylic acid and a polymer thereof.

From the viewpoint of increasing the yield of the (meth) acrylic acid, the trimer to pentadecamer of the 3-hydroxycarboxylic acid polymer preferably constitute the same amount as that described above for the second aspect of the present invention, of a total of 100% by mass of the 3-hydroxycarboxylic acid and a polymer thereof.

From the viewpoints of increasing the yield of the (meth) acrylic acid, the trimer to nonamer of the 3-hydroxycarboxylic acid polymer preferably constitute the same amount as that described above for the first aspect of the present invention, of a total of 100% by mass of the 3-hydroxycarboxylic acid and a polymer thereof.

Also, the eicosamer or higher order units of the 3-hydroxycarboxylic acid polymer preferably constitute the same amount as described above for the second aspect of the present invention, of a total of 100% by mass of the 3-hydroxycarboxylic acid and a polymer thereof.

Here, the decomposed products of the polymer refer to products with a decreased degree of polymerization obtained by heating the polymer to decompose the ester bonds, depolymerizing the polymer.

For example in the case of a decomposed product of a 3HP polymer, an example of the decomposed product is a polyester of 3HP represented by the following formula (2) with a lower degree of polymerization than the material polymer. Also, the decomposed product can be a compound represented by the following formula (3) which is obtained by decomposing the polymer and has a double bond at each end and has a lower degree of polymerization than the material polymer.

[Chem. 2]

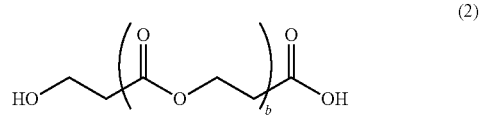

(2)

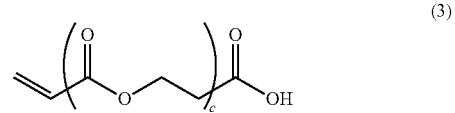

(3)

Here, the polymer and the decomposed product of the polymer each have distributed degrees of polymerization, not a single degree of polymerization, and thus each of a, b, and c represents an average degree of polymerization. Since the decomposed product of the polymer has a lower degree of polymerization than the material polymer, the inequalities of a>b and a>c hold.

The b and c in the formula (2) and the formula (3) each are 0 to 10. From the viewpoints of ease of evaporation, improvement of the yield of the acrylic acid, and suppression of generation of heavy substances on the dehydration catalyst and a decrease in the catalytic activity, the b and c each are preferably 0 to 8, more preferably 0 to 5, still more preferably 0 to 3, and particularly preferably 0 to 2.

The decomposition of the polymer into low molecular components through the decomposition step generates 3HP (b=0 in formula (2)), 3HP dimers (b=1 in formula (2)), 3HP trimers (b=2 in formula (2)), 3HP tetramers (b=3 in formula (2)), acrylic acid (c=0 in formula (3)), acrylic acid dimers (c=1 in formula (3)), acrylic acid trimers (c=2 in formula (3)), and acrylic acid tetramers (c=3 in formula (3)).

The decomposition step may remove the hydroxyl groups from the 3HP and the 3HP polymer to form double bonds, depending on the reaction conditions. For example, reactions such as acrylic acid generation from 3HP, acrylic acid dimer generation from 3HP dimers, and acrylic acid trimer generation from 3HP trimers may proceed. These products generated are the same compounds as the decomposed products of the above polymer, and can contribute to generation of acrylic acid, the target product. Hence, the products generated are included in decomposed products of a polymer in the present invention. The ester bonds of the multimers of the acrylic acid generated by the above reaction route may be decomposed to produce a product with an even lower degree of polymerization.

However, at this stage, the yield of the acrylic acid, the target component, is not yet satisfactory. The product obtained in the decomposed step is therefore further brought into contact with a dehydration catalyst in the dehydration step, so that acrylic acid is generated from 3HP. Thereby, the yield of the acrylic acid at the end of the dehydration step is very high.

Depolymerization of the polymer as described above leads to dehydration of 3HP which generates acrylic acid in the dehydration step. In addition, the following effects are expected. For example, bringing a decomposed product having a low degree of polymerization (dimer, trimer, tetramer of acrylic acid) into contact with a dehydration catalyst under the later-described conditions may decompose these multimers, so as to produce acrylic acid. Also, bringing a decomposed product having a low degree of polymerization (dimer, trimer, and tetramer of 3HP) into contact with a dehydration catalyst under the later-described conditions may generate 3HP and acrylic acid, and acrylic acid may be further generated from the generated 3HP through the dehydration reaction. Accordingly, the yield of the acrylic acid is further improved.

In the following, a decomposition step of generating a material composition containing a 3-hydroxycarboxylic acid polymer and decomposed products of the polymer, and a dehydration step of generating (meth)acrylic acid by bringing the decomposed product into contact with a dehydration catalyst are described in the stated order.

The material composition containing a 3-hydroxycarboxylic acid polymer may contain a solvent. The specific examples and preferred examples of the solvent, and the preferred concentration of the solvent such as water are the same as those described above for the first aspect of the present invention.

The 3-hydroxycarboxylic acid used in the present invention can be obtained from various resources, but the production method and the suitable method are the same as those described above for the first aspect of the present invention. Also, as described above, the 3-hydroxycarboxylic acid can be obtained by a known method.

It is also possible to produce a 3-hydroxycarboxylic acid polymer from a microorganism, and the polymer may be used as a material composition.

The material composition containing a 3-hydroxycarboxylic acid polymer used in the present invention is preferably a material composition with a smaller amount of impurities. The method for obtaining a material composition with a small amount of impurities is the same as that described above for the first aspect of the present invention.

As described above, in the case of producing 3-hydroxycarboxylic acid by fermentation, a purification step of removing the impurities resulting from the fermentation is preferably performed. Since the concentration of the 3-hydroxycarboxylic acid in the fermented mash is not high, use of the fermented mash with such a concentration in the step of producing (meth)acrylic acid may require an excessive amount of energy for heating or require a large reactor, leading to an increase in the cost. In this respect, the purification step and the condensation step of the 3-hydroxycarboxylic acid from the fermented mash are preferably performed. Still, heating in these steps or an increase in the concentration of the 3-hydroxycarboxylic acid due to condensation definitely generates a 3-hydroxycarboxylic acid polymer. Therefore, the method for producing (meth)acrylic acid with a high yield from a material composition containing a 3-hydroxycarboxylic acid polymer is industrially very important.

The decomposition step of decomposing a 3-hydroxycarboxylic acid polymer is performed by heating the starting material containing 3-hydroxycarboxylic acid polymer.

The heating can be performed in the presence or absence of a catalyst.

The preferred decomposition temperature in the case of performing the decomposition step in the absence of a catalyst and the preferred decomposition temperature in the case of performing the decomposition step in the presence of a catalyst are respectively the same as the preferred heating temperature in the case of performing the heating step in the absence of a catalyst and the preferred heating temperature in the case of performing the heating step in the presence of a catalyst which have been described above for the first aspect of the present invention.

The catalyst used in the decomposition step (hereinafter, also referred to as a decomposition catalyst) is not particularly limited if the catalyst is capable of decomposing a 3-hydroxycarboxylic acid polymer, and examples thereof include acid catalysts and basic catalysts. In particular, solid acid catalysts and solid basic catalysts are preferred.

The residence time in the decomposition reactor is preferably 5 seconds to 5 hours, although depending on the structure of the decomposition reactor. The residence time is more preferably 10 seconds to 3 hours. Too short a residence time may cause insufficient decomposition, while too long a residence time may cause a side reaction, possibly decreasing the final yield of the (meth)acrylic acid.

A low pressure in the decomposition reactor is advantageous because evaporation of the decomposed product is more likely to occur as the pressure decreases. Still, the pressure needs to be selected in consideration of the appropriate pressure for the dehydration reactor in the subsequent process and the cost for the instruments and the like. The preferred range of the pressure in the decomposition reactor is the same as the preferred range of the pressure in the heater described above for the first aspect of the present invention.

The preferred structure, specific examples, and the use method of the decomposition reactor, and the kind and materials of the packing to be charged into the channels for the material composition are the same as those described above for the heater in the first aspect of the present invention. Here, the statement should be read by replacing the word "heating" with "decomposition".

In this way, low molecular components generated upon decomposition of the 3-hydroxycarboxylic acid polymer in the decomposition reactor are sent to the next dehydration step together with the low molecular components contained in the material composition, such as the solvent and the 3-hydroxycarboxylic acid. At this time, the mixture containing low molecular components generated upon decomposition of the 3-hydroxycarboxylic acid polymer at the outlet of the decomposition reactor is preferably in the gaseous state through evaporation in the decomposition reactor. Bringing the gaseous mixture into contact with a dehydration catalyst can suppress clogging or the like phenomena in the dehydration reactor.

In order to facilitate evaporation of the decomposed product, the decomposition step may be performed in the presence of an inert gas. The Specific examples, the preferred embodiments, and the preferred amount of supply of the inert gas are the same as those described above for the heating step in the first aspect of the present invention.

In the case that the material composition contains water, the vapor generated by evaporation of the water in the decomposition step is included in the inert gas.

The reactor used in the dehydration step, and the preferred kinds and use method of the reactor are the same as those described above for the first aspect of the present invention. The vapor of the material composition supplied can be the outlet gas from the decomposition reactor.

The dehydration step may be performed at any time after the decomposition step, and other step(s) may be performed between these steps. For example, the outlet gas from the decomposition reactor may be subjected to a temperature control step of heating or cooling the gas to a predetermined temperature, and then subjected to the dehydration step in the reactor.

Also, the decomposition reactor and the reactor may be integrated into one machine. For example, one preferred embodiment is an operation using a reaction tube in which packing having a large surface area is charged as a decomposition layer and a catalyst is charged under the decomposition layer so that the decomposition step is performed on the decomposition layer and then the dehydration step is performed on the catalyst layer.

Another preferred embodiment is an operation using a single or multiple decomposition layers connected to the multi-tubular reactor filled with a catalyst.

The specific examples of the dehydration catalyst, the shape of the molded body in the case that the dehydration catalyst is a catalyst molded body, and the other conditions are the same as those described above for the first aspect of the present invention.

The specific surface area determined by the BET method, the Hammett acidity function $H_0$, and the size of the catalyst each are the same as that described above for the first aspect of the present invention.

The preferred range of the temperature of the catalyst layer is the same as that described above for the first aspect of the present invention.

The reaction pressure is not particularly limited, and can be determined in consideration of conditions such as the method for decomposing the material composition, the productivity of the dehydration reaction, and the collection efficiency after the dehydration. The preferred range of the reaction pressure is the same as that described above for the first aspect of the present invention.

The dehydration reaction can be performed by bringing a dehydration catalyst into contact with 3-hydroxycarboxylic acid or a 3-hydroxycarboxylic acid depolymerized polymer obtained by depolymerizing a material composition containing a 3-hydroxycarboxylic acid polymer in a decomposition reactor. Here, the 3-hydroxycarboxylic acid and 3-hydroxycarboxylic acid polymer are preferably in a gaseous state when brought into contact with the dehydration catalyst. If the 3-hydroxycarboxylic acid and 3-hydroxycarboxylic acid polymer are in a liquid state when brought into contact with the dehydration catalyst, clogging in the reactor and rapid deterioration in the catalytic activity due to generation of heavy components may occur. Although the reaction may be performed at higher temperatures to suppress such phenomena, but in this case, problems may be caused such as a decrease in the yield of the (meth)acrylic acid or an increase in the amount of impurities due to excessive decomposition of the materials and the products, a decrease in the catalytic activity due to an increase in the coking on the catalyst, and an irreversible decrease in the catalytic activity due to a structural change in the catalyst or scattering of the catalyst components.

Depolymerization of a 3-hydroxycarboxylic acid polymer in a decomposition reactor allows easy evaporation of the decomposed products. Also, the dehydration reaction of the 3-hydroxycarboxylic acid and the polymer thereof removing the hydroxy groups to form double bonds in the decomposition reactor also decreases the boiling temperature to allow easy evaporation. As described above, it is possible to avoid such problems, which leads to a stable, long-term dehydration reaction.

With the decomposition step and the dehydration step, the production of (meth)acrylic acid from a material composition containing a 3-hydroxycarboxylic acid polymer can be kept stable. Still, the carbonous substances may gradually be accumulated inside the decomposition reactor, inside the reactor, or on the catalysts. In this case, problems may arise such as clogging in the instruments (e.g. decomposition reactor, reactor, tubes), a decrease in the decomposition efficiency due to a decrease in the thermal conduction efficiency of the decomposition reactor, and a decrease in the productivity or the selectivity due to a decrease in the catalytic activity. In that case, removal of the generated carbonous substances restores the normal conditions.

The method for catalyst regeneration is the same as the methods described in the first and second aspects of the present invention.

In the present invention, the method for obtaining a composition containing (meth)acrylic acid by cooling the reaction product obtained at the reactor outlet, and the preferred concentration of the (meth)acrylic acid in the composition are the same as those described above for the first aspect of the present invention.

In a composition of the reaction product obtained thereby contains water and (meth)acrylic acid which are main reaction products, and may also contain by-products, and the solvent and impurities in the material composition. If the solvent is water, the composition can be used as a starting material for producing a polymer in the state of an aqueous solution of (meth)acrylic acid. Also, addition of the purification step enables production of (meth)acrylic acid with high purity. The specific examples and the preferred embodiments of the purification step are the same as those described above for the first aspect of the present invention.

After separation of the (meth)acrylic acid in, for example, the purification step described above from the product obtained by the process including the decomposition step and the dehydration step, the remaining impurities can be reused by recycling. For example, the yield of the (meth) acrylic acid can be increased by reusing the 3-hydroxycarboxylic acid, the 3-hydroxycarboxylic acid polymer represented by the formula (2), and the (meth)acrylic acid polymer represented by the formula (3) as starting materials in the decomposition step and the dehydration step. The details are described later.

<Recycling Step>

The step of reusing impurities (recycling step) as descried later is suitably applicable to any of the methods for producing (meth)acrylic acid of the first to third aspects of the present invention. In other words, the methods for producing (meth)acrylic acid according to the first to third aspects of the present invention each preferably include the step of reusing impurities. The impurities here refer to substances that are contained in the reaction product and can be materials of (meth)acrylic acid, namely 3-hydroxycarboxylic acid, a 3-hydroxycarboxylic acid polymer, and a (meth) acrylic acid polymer. For example, the 3-hydroxycarboxylic acid and the oligomers remaining after the end of the reaction are preferably reused as materials in each step.

Hereinafter, drawings illustrating reaction formulas relative to the methods for producing (meth)acrylic acid according to the first to third aspects of the present invention, and drawings illustrating formulas in which the recycling step is added to the above reaction formulas are described.

Figure 2:
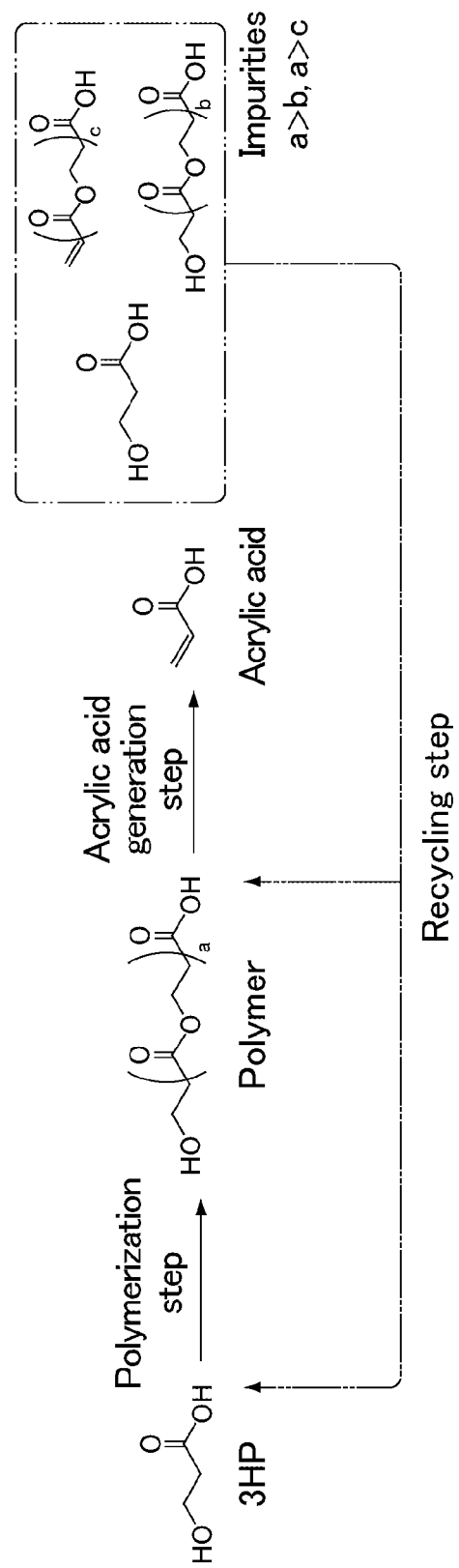
FIG. 2 is a view illustrating steps of further recycling impurities from the reaction in FIG. 1.

FIG. 1 is a view illustrating a reaction formula with 3HP as a starting material according to the production method of the first aspect of the present invention. The reaction formula illustrated in FIG. 1 includes a polymerization step and an acrylic acid generation step. FIG. 2 is a view illustrating steps of further recycling impurities from the reaction in FIG. 1. In the reaction steps according to the present invention, acrylic acid is generated as a main product, and impurities such as 3HP and depolymerized oligomers (compared to the starting material) may remain. The reaction formula illustrated in FIG. 2 reuses the impurities remaining after the acrylic acid generation step as starting materials in the polymerization step and the acrylic acid generation step. The impurities are preferably reused as starting materials in the steps as described above. The same applies to the following reaction formulas.

Figure 3:
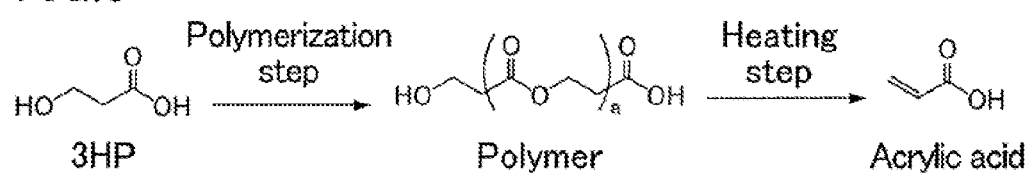
FIG. 3 is a view illustrating a reaction formula with 3HP as a starting material according to the production method of a second aspect of the present invention.
Figure 4:
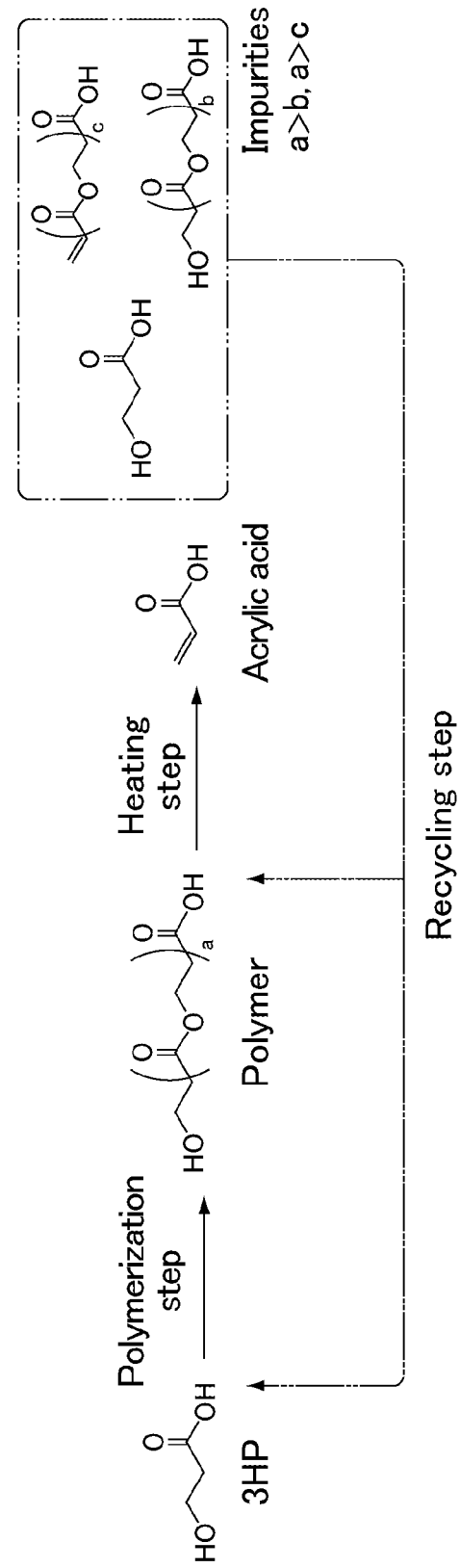
FIG. 4 is a view illustrating steps of further recycling impurities from the reaction in FIG. 3.

FIG. 3 is a view illustrating a reaction formula with 3HP as a starting material according to the production method of the second aspect of the present invention. The reaction formula illustrated in FIG. 3 includes the polymerization step and the heating step. FIG. 4 is a view illustrating steps of recycling impurities from the reaction in FIG. 3. The reaction formula illustrated in FIG. 4 reuses the impurities remaining after the heating step as starting materials in the polymerization step and the heating step.

Figure 5:
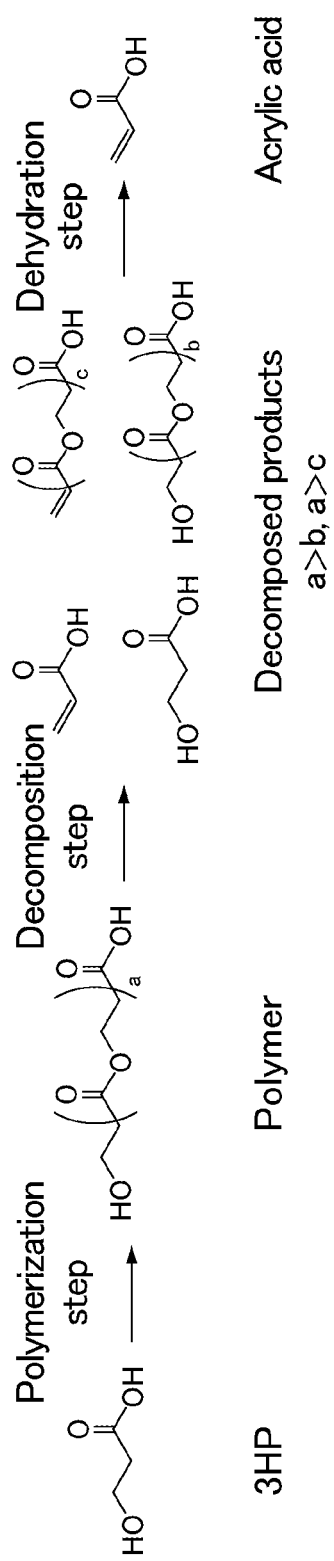
FIG. 5 is a view illustrating a reaction formula with 3HP as a starting material according to the production method of a third aspect of the present invention.
Figure 6:
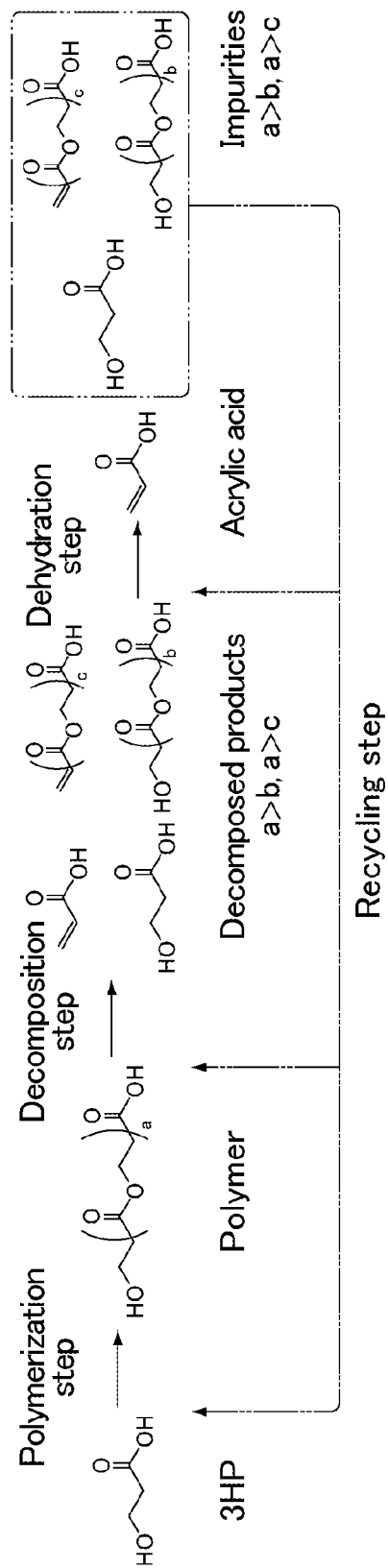
FIG. 6 is a view illustrating steps of further recycling impurities from the reaction in FIG. 5.

FIG. 5 is a view illustrating a reaction formula with 3HP as a starting material according to the production method of the third aspect of the present invention. The reaction formula illustrated in FIG. 5 includes a polymerization step, a decomposition step, and a dehydration step. FIG. 6 is a view illustrating steps of further recycling impurities from the reaction in FIG. 5. The reaction formula illustrated in FIG. 6 reuses the impurities remaining after the dehydration step as starting materials in the polymerization step, the decomposition step and the dehydration step. FIG. 5 and FIG. 6 are also views illustrating preferred examples of the reaction formula with 3HP as a starting material according to the production methods of the first and second aspects of the present invention. The reaction formulas illustrated in FIG. 1 to FIG. 6 use 3HP as a starting material.

Figure 7:
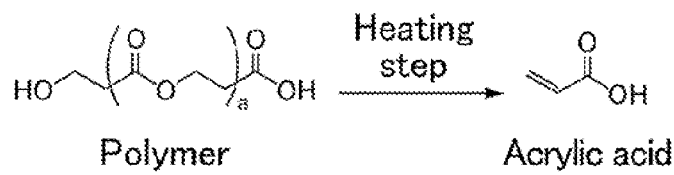
FIG. 7 is a view illustrating a reaction formula with a 3HP polymer as a starting material according to the production method of the second aspect of the present invention.
Figure 8:
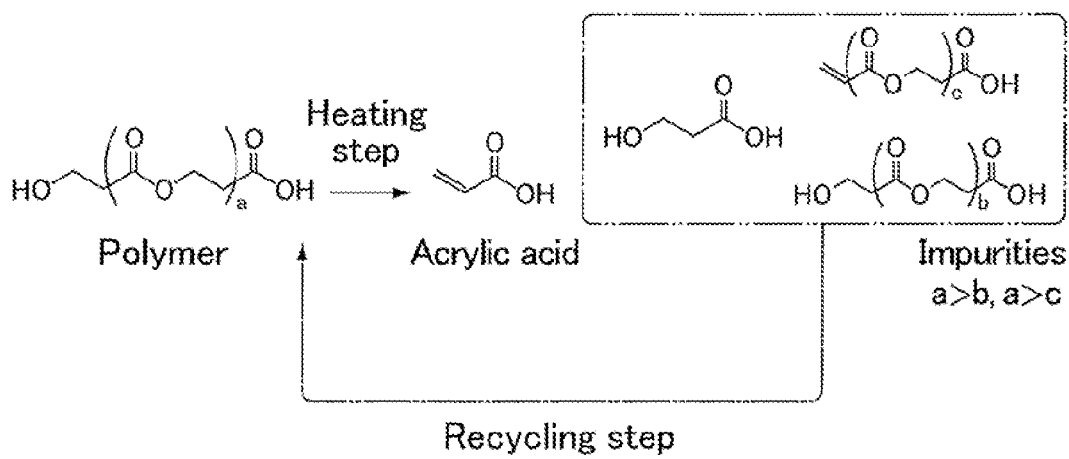
FIG. 8 is a view illustrating steps of further recycling impurities from the reaction in FIG. 7.

FIG. 7 is a view illustrating a reaction formula with a 3HP polymer as a starting material according to the production method of the second aspect of the present invention. The reaction formula illustrated in FIG. 7 excludes the polymerization step and includes the heating step, unlike the reaction formula illustrated in FIG. 3. Even with such a reaction formula, the effect of the second aspect of the present invention can substantially be achieved. FIG. 8 is a view illustrating steps of further recycling impurities from the reaction in FIG. 7. The reaction formula illustrated in FIG. 8 reuses the impurities remaining after the heating step as starting materials in the heating step.

Figure 9:
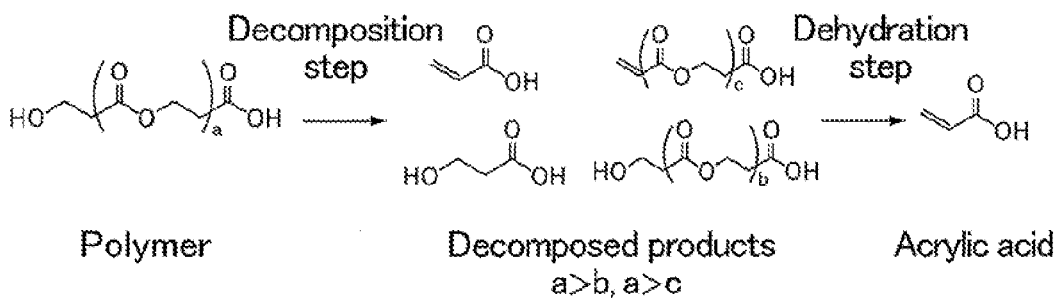
FIG. 9 is a view illustrating a reaction formula with a 3HP polymer as a starting material according to the production method of the third aspect of the present invention.
Figure 10:
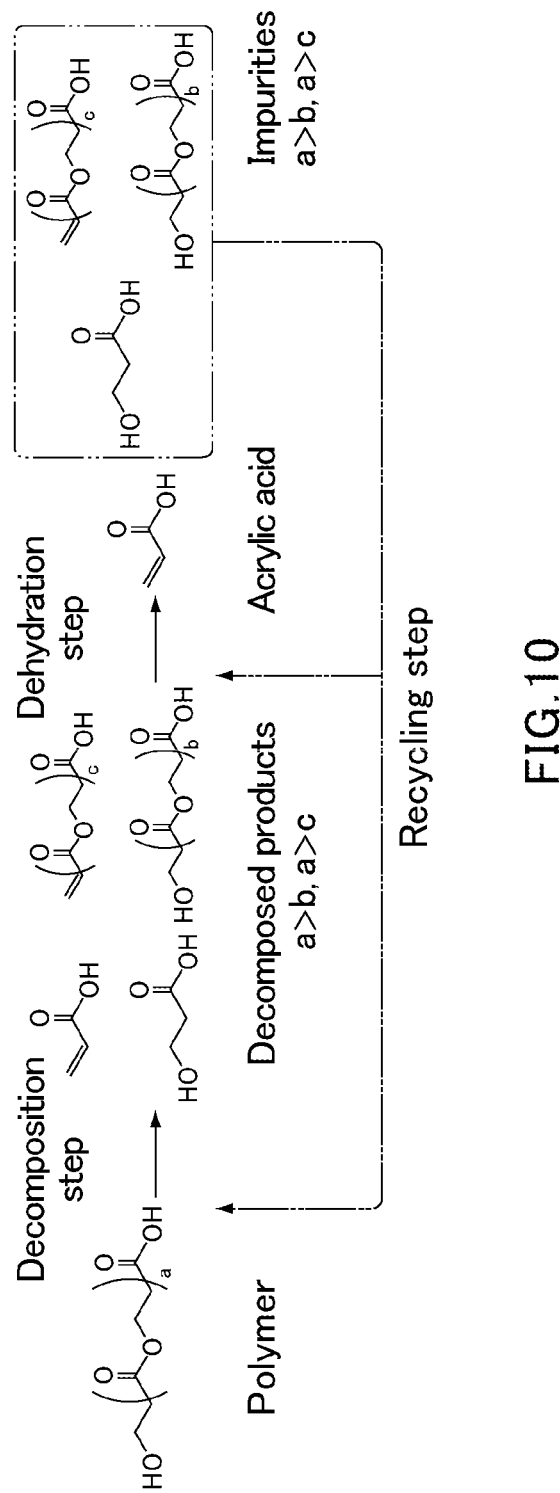
FIG. 10 is a view illustrating steps of further recycling impurities from the reaction in FIG. 9.

FIG. 9 is a view illustrating a reaction formula with a 3HP polymer as a starting material according to the production method of the third aspect of the present invention. The reaction formula illustrated in FIG. 9 excludes the polymerization step and includes the decomposition step and the dehydration step, unlike the reaction formula illustrated in FIG. 5. Even with such a reaction formula, the effect of the third aspect of the present invention can substantially be achieved. FIG. 10 is a view illustrating steps of recycling impurities from the reaction in FIG. 9. The reaction formula illustrated in FIG. 10 reuses the impurities remaining after the dehydration step as starting materials in the decomposition step and the dehydration step.

The reaction formulas illustrated in FIG. 7 to FIG. 10 described above use a material composition containing a 3HP polymer (oligomer).

Figure 11:
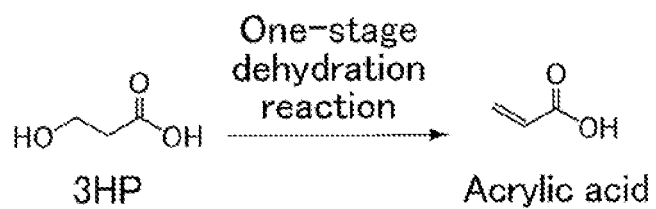
FIG. 11 is a view illustrating a reaction formula with 3HP as a starting material according to a conventional method for producing acrylic acid.

The reaction step of obtaining acrylic acid through a one-stage dehydration reaction from 3HP as illustrated in FIG. 11 is a known reaction step.

In particular, in the case of a reaction formula with neither the decomposition step nor the dehydration step, for example in the case that the acrylic acid generation step for the reaction formula illustrated in FIG. 1, the heating step for the reaction formula of FIG. 3 or the heating step for the reaction formula illustrated in FIG. 7 is performed as a one-stage reaction, the residual amount of the impurities after the reaction is usually large compared to the case of performing both the decomposition step and the dehydration step for the reaction formula. Hence, performing the step of reusing impurities is particularly preferred because the effect of increasing the yield of the acrylic acid is significant. In other words, if (meth)acrylic acid is produced through only one-stage reaction from a composition containing a 3-hydroxycarboxylic acid polymer, such as the case of performing the decomposition step but not the dehydration step, the impurities after the reaction are particularly preferably reused as described above.

<Method for Producing Hydrophilic Resin>

The methods for producing a hydrophilic resin according to the first to third aspects of the present invention feature polymerization of monomeric components containing (meth)acrylic acid obtained by the method for producing (meth)acrylic acid described above. That is, the (meth) acrylic acid obtained by the production method of the present invention can be used as a starting material of a hydrophilic resin such as a water-absorbing resin and a water-soluble resin. Here, the polymerization step of polymerizing 3-hydroxycarboxylic acid to generate a composition containing a 3-hydroxycarboxylic acid polymer is also referred to as a first polymerization step, and the polymerization step of polymerizing a monomeric component containing (meth)acrylic acid obtained by the production method of the present invention to generate a hydrophilic resin is also referred to as a second polymerization step.

In the case of using the (meth)acrylic acid obtained by the production method of the present invention as a starting material for producing a hydrophilic resin such as a water-absorbing resin and a water-soluble resin, the use makes it easy to control the polymerization reaction, stabilizes the qualities of the obtained hydrophilic resin, and improves the properties such as water-absorption ability and dispersibility of inorganic materials.

The hydrophilic resin is preferably a water-absorbing resin.

A water-absorbing resin can be produced by, for example, performing cross-linking polymerization of (meth)acrylic acid obtained by the production method of the present invention and/or a salt thereof (a salt obtained by partially neutralizing the (meth)acrylic acid) as main components (constituting preferably 70 mol % or more, more preferably 90 mol % or more) of the monomeric component, about 0.001 to 5 mol % (based on the (meth)acrylic acid) of a crosslinking agent, and about 0.001 to 2 mol % (based on the monomeric component) of a radical polymerization initiator; and drying and grinding the cross-linked polymer.

Here, the water-absorbing resin is water-swelling, water-insoluble poly(meth)acrylic acid having a cross-linked structure, which generates water-insoluble hydrogel with preferably 25% by mass or less, more preferably 10% by mass or less, of a water-soluble component (water-soluble content), by absorbing pure water or physiological saline in an amount of three times or more, preferably 10 times to 1000 times, of the self-weight.

Specific examples and the methods for determining the physical properties of such a water-absorbing resin are described in, for example, U.S. Pat. No. 6,107,358, U.S. Pat. No. 6,174,978, and U.S. Pat. No. 6,241,928. The preferred production methods from the viewpoint of increasing the productivity are described in, for example, U.S. Pat. No. 6,867,269, U.S. Pat. No. 6,906,159, U.S. Pat. No. 7,091,253, WO 2001/038402, and WO 2006/034806.

The sequence of steps of producing a water-absorbing resin using (meth)acrylic acid as a starting material through processes such as neutralization, polymerization, and drying is as described below, for example.

Part of the (meth)acrylic acid obtained by the production-method of the present invention is supplied to the process of producing a water-absorbing resin through a line. A water-absorbing resin is produced by introducing the (meth)acrylic acid to the neutralization step, polymerization step, and drying step for the desired treatment. The desired treatments may be performed to improve the physical properties, and a cross-linking step may be performed during or after the polymerization, for example.

The neutralization step is an optional step, and may be performed by, for example, a method of mixing a predetermined amount of powder or an aqueous solution of a basic substance with (meth)acrylic acid or poly(meth)acrylic acid (salt). The method may be any known method. The neutralization step may be performed before or after the polymerization, or may be performed both before and after the polymerization.

The basic substance used for neutralization of the (meth) acrylic acid or poly(meth)acrylic acid (salt) is, for example, a known appropriate basic substance such as (hydrogen) carbonate, a hydroxide of an alkali metal, ammonia, and organic amine.

Also, the degree of neutralization of the poly(meth)acrylic acid is not particularly limited, and may be controlled to any value (for example, any value in the range of from 30 to 100 mol %).

The polymerization method in the polymerization step is not particularly limited, and may be any known polymerization method such as polymerization with a radical polymerization initiator, radiation polymerization, polymerization through irradiation of electron rays or active energy rays, and ultraviolet polymerization using a photosensitizer. The conditions such as the polymerization initiator and the polymerization conditions can be optionally selected. Of course, known additive(s) such as a cross-linking agent, other monomers, water-soluble chain transfer agents, and hydrophilic polymers may be added according to need.

The (meth)acrylate polymer after the polymerization (namely, water-absorbing resin) is then subjected to the drying step. The drying method is not particularly limited, and may be any appropriate drying using a known drying device (e.g. hot-air dryer, fluidized-bed dryer, Nauta dryer) at a desired drying temperature, preferably at 70° C. to 230° C. The water-absorbing resin obtained through the drying step may be used without any further treatment or after being pelletized and ground into a desired shape and subjected to surface crosslinking, or may be used after being subjected to post-treatment suited to the use, such as addition of a known additive (e.g. reducing agent, flavor, binder).

The step of generating (meth)acrylic acid in the method for producing a hydrophilic resin in the present invention may be any preferred appropriate method such as the methods for producing (meth)acrylic acid of the first to third aspects of the present invention described above.

The present invention relates to a method for producing a composition containing a hydrophilic resin from 3-hydroxycarboxylic acid obtained by fermentation, and also a method for producing a composition containing 10 ppm by mass or less of (meth)acrylamides in the hydrophilic resin. The present invention also relates to a composition containing a hydrophilic resin in which the amount of the (meth)acrylamides was reduced. The preferred upper limit for the amount of (meth)acrylamides in the composition is the same as the preferred upper limit for the amount of the (meth) acrylamides described above for the method for producing (meth)acrylic acid of the present invention.

The present invention also relates to a resin composition containing a hydrophilic resin, which contains a nitrogen-containing compound that gives an amount of nitrogen of 80 ppm by mass or less based on the hydrophilic resin. The resin composition of the present invention is preferably obtained by the method for producing a resin composition of the present invention. The method for producing a resin composition can be any of the preferred appropriate embodiments described herein. In particular, a method for producing a resin composition including a fermentation step wherein 3-hydroxycarboxylic acid as a starting material is generated is particularly preferred. Thereby, a hydrophilic resin can be produced from a renewable resource, and the amount of nitrogen in a nitrogen-containing compound (e.g. (meth)acrylamides) in the composition can be reduced, so that the composition can be suitably used in various applications. This is a significant effect that could not have been achieved by the conventional techniques.

EXAMPLES

Hereinafter, the present invention is described in more detail with examples. The present invention, however, is not limited by the following examples, and can be performed by appropriately making changes as long as the consistency is maintained in the contents of the description. All of these changes is also included in the technical scope of the present invention.

In the following, "%" refers to "% by mass", and "part(s)" refer(s) to "part(s) by weight", unless otherwise specified. Also, in Table 1, "dimer" to "eicosamer" refers to "dimer to eicosamer" of 3HP.

Liquid chromatography analysis and the like in the following preparations, examples, and comparative examples were performed under the following conditions.
(Analysis Condition of Liquid Chromatography)
  Column used: Inertsil ODS-4 (from GL Sciences Inc.)×2
  Eluent: Acetonitrile/water/phosphoric acid/potassium dihydrogen phosphate=35/64/0.7/0.3 (ratio by weight)
  Detector: UV 205 nm
  Column temperature: 50° C.
(Analysis Condition of Size Exclusion Chromatography)
  Column used: TSKgel Super H200 (from TOSOH CORP.)
  Solvent: tetrahydrofuran
  Detector: UV 205 nm
  Column temperature: 40° C.
(Analysis Condition of Gas Chromatography)
  Column: DB-WAX (from Agilent Technologies) 30 m
  Injector: 300° C.
  Detector: FID, 300° C.
  Column temperature: 40° C.→300° C.

The yield of the acrylic acid in the following examples was determined based on the following definition.

Yield (mol %) of acrylic acid=100×(number of moles of generated acrylic acid)/(number of moles of supplied 3-hydroxycarboxylic acid units)

The number of moles of 3-hydroxycarboxylic acid units=(number of moles of 3-hydroxycarboxylic acid+number of moles of dimer×2+number of moles of trimer×3+number of moles of tetramer×4+number of moles of pentamer×5+number of moles of hexamer×6+number of moles of heptamer×7+number of moles of octamer×8+number of moles of nonamer×9+weight (g) of decamer or higher order units/72)

(Preparation of Dehydration Catalyst [Crushed Catalyst])

Potassium nitrate (1.7 g) and diammonium hydrogen phosphate (1.1 g) were dissolved in water (100 g), and then silicon oxide (20 g) was added to the solution with stirring at 90° C. The resulting mixture was concentrated to dryness, and dried in the air at 120° C. for 20 hours. The obtained solid was coarse ground, and calcined in the air at 500° C. for 2 hours, whereby a catalyst with a formulation (except for oxygen) of $K_1P_{0.5}Si_{20}$ was obtained. The obtained catalyst was crushed to 10 to 24 mesh, and used for dehydration.
(Preparation of a Dehydration Catalyst [Molded Catalyst])

Potassium nitrate (17 g) and diammonium hydrogen phosphate (11 g) were dissolved in water (1000 g), and then silicon oxide (200 g) was added to the solution with stirring at 90° C. Water was evaporated from the mixture, so that the mixture was concentrated. The obtained mixture was formed into a ring-shaped molded body with an extruder. The molded body was dried in the air at 120° C. for 20 hours, and calcined in the air at 500° C. for 2 hours. Thereby, a molded catalyst with a formulation (except for oxygen) of $K_1P_{0.5}Si_{20}$ was obtained. The ring-shaped molded catalyst had a size of 6 mm in outer diameter, 2 mm in inner diameter, and 7 mm in height.
(Preparation 1 of Material 3HP)

In accordance with the method of Example 1 described in JP 2012-085635 A, 3HP was prepared by fermentation. Bacterial cells were isolated from the obtained fermented mash by filtration. To the filtrate (700 g), n-dodecanol (100 g) was added, and water was removed with a rotary evaporator. The evaporation was performed until there was no distillate at 50° C. and 2.7 kPa.

The obtained residual liquid was put into a thin-film evaporator (80° C., 10 Pa), and the mixture of 3HP and n-dodecanol was obtained as a distillate. To the obtained distillate was added an equivalent amount of water. They were mixed, and 3HP was extracted to the water phase. To the oil phase obtained by oil-water separation, an equivalent amount of water was added again so that 3HP was extracted. The water phase obtained by oil-water separation was mixed and the resulting mixture was filtered, so that an aqueous solution of 3HP was obtained. The concentration of 3HP was 16% by mass.
(Preparation 2 of Material 3HP)

In accordance with the method of Example 1 described in JP 2012-085635 A, 3HP was prepared by fermentation. Bacterial cells were isolated from the obtained fermented mash by filtration. To the liquid from which the bacterial cells were removed, a six-fold amount of tridecylamine and an equivalent amount of dodecanol were added. The mixture was heated to 85° C. under reduced pressure, so that low-boiling components such as water were distilled off. The resulting organic phase was mixed with a ⅕-volume of water, and the mixture was heated to 140° C. for oil-water separation. Further filtration was performed, so that an aqueous solution containing 3-hydroxypropionic acid (3HP crude solution) was obtained.
(Preparation of Composition Containing 3HP Polymer)

With the aqueous solution of 3HP having a concentration of 16% by mass obtained as described in the above (Preparation 1 of material 3HP), material solutions as compositions containing a 3HP polymer (material 1-1 to material 1-3, material 2-1 to material 2-3, material 3-1, material 3-2) were prepared by the corresponding method shown in Table 1. Also, a material solution as a composition containing a 3HP polymer (material 1-4) was prepared in the same manner as that for material 1-3, except that the 3HP crude solution obtained in the above (Preparation 2 of material 3HP) was used in place of the aqueous solution of 3HP having a concentration of 16% by mass. For these material solutions, 3HP and oligomers from dimer to nonamer were analyzed by liquid chromatography, and decamer or higher order polymer were analyzed by size exclusion chromatography. The formulations of the material solutions are shown in Table 1.

In any of the material solutions shown in Table 1, 21-mer or higher order polymer units were not detected. Although Table 1 shows the total amount of trimer or higher order units of the 3HP polymer for each material solution, the total amount is the same as the total amount of trimer to eicosamer of the 3HP polymer.

Here, the total mass of 3HP is 80.7% by mass when the oligomers are calculated in terms of 3HP monomers by hydrolyzing the oligomers from dimer to nonamer of the material 1-1 into 3HP monomers. Meanwhile, hydrolysis of the oligomers consumes water, and thus the amount of water is considered to decrease from 27% by mass to 19.7% by mass. Hence, the solution is considered to be an aqueous solution of 3HP having a concentration of about 80% by mass.

The amounts of nitrogen in the material 1-3 and the material 1-4 measured were respectively 150 ppm by mass and 0.25% by mass based on 3HP and the 3HP polymer.

(Preparation of Material 2-4)

The prepared material 2-3 was placed in a reactor, and antimony trioxide was added thereto as a catalyst, so that the material 2-3 was further polymerized. The temperature was gradually raised, and water generated was removed while the pressure was further reduced. The material was eventually held at 260° C. and 100 Pa for 5 hours. The obtained polymer was analyzed by liquid chromatography, but 3HP and oligomers from dimer to nonamer were not detected. The polymer was found to have an average molecular weight of 8000 as a result of analysis by size exclusion chromatography. The polymer contained 2.5% by mass of decamer to eicosamer. The obtained polymer was ground and suspended in water to give a 50% by mass slurry, which was used as the material 2-4. Accordingly, the total amount of trimer to eicosamer of 3HP polymer was 2.5% by mass based on the total amount of 3HP and the 3HP polymer.

TABLE 1

|  | Material 1-1 | Material 1-2 | Material 1-3 | Material 1-4 |
|---|---|---|---|---|
| Concentration (% by mass) | | | | |
| $H_2O$ | 27% by mass | 20% by mass | 23% by mass | 23% by mass |
| 3HP | 28% by mass | 77% by mass | 54% by mass | 54% by mass |
| Dimer | 21% by mass | 2% by mass | 17% by mass | 17% by mass |
| Trimer | 12% by mass | 1% by mass | 4% by mass | 4% by mass |
| Tetramer | 7% by mass | 0% by mass | 1% by mass | 1% by mass |
| Pentamer | 3% by mass | 0% by mass | 0% by mass | 0% by mass |
| Hexamer | 2% by mass | 0% by mass | 0% by mass | 0% by mass |
| Heptamer | 1% by mass | 0% by mass | 0% by mass | 0% by mass |
| Octamer | 0.4% by mass | 0% by mass | 0% by mass | 0% by mass |
| Nonamer | 0.2% by mass | 0% by mass | 0% by mass | 0% by mass |
| Decamer | 0% by mass | 0% by mass | 0% by mass | 0% by mass |
| Undecamer | 0% by mass | 0% by mass | 0% by mass | 0% by mass |
| Dodecamer | 0% by mass | 0% by mass | 0% by mass | 0% by mass |
| Tridecamer | 0% by mass | 0% by mass | 0% by mass | 0% by mass |
| Tetradecamer to eicosamer | 0% by mass | 0% by mass | 0% by mass | 0% by mass |
| Total amount of timer or higher order units/ (3HP + 3HP polymer) | 34% by mass | 1.3% by mass | 6.5% by mass | 6.5% by mass |
| Methods for preparing material mixture from 16% by mass 3HP aqueous solution | Condensed with rotary evaporator (*1). | Condensed with thin-film evaporator (*2). | Obtained the material 1-2 by the same methods as the preparation method for material 1-2, stored the material 1-2, and oligomerized the material 1-2 (*3). | — |

|  | Material 2-1 | Material 2-2 | Material 2-3 | Material 3-1 | Material 3-2 |
|---|---|---|---|---|---|
| Concentration (% by mass) | | | | | |
| $H_2O$ | 77% by mass | 52% by mass | 13% by mass | 19% by mass | 11% by mass |
| 3HP | 18% by mass | 30% by mass | 19% by mass | 23% by mass | 15% by mass |
| Dimer | 3.5% by mass | 12% by mass | 19% by mass | 21% by mass | 17% by mass |
| Trimer | 0.5% by mass | 4% by mass | 16% by mass | 15% by mass | 15% by mass |
| Tetramer | 0% by mass | 1% by mass | 12% by mass | 10% by mass | 13% by mass |
| Pentamer | 0% by mass | 0% by mass | 8% by mass | 5% by mass | 9% by mass |
| Hexamer | 0% by mass | 0% by mass | 6% by mass | 3% by mass | 6% by mass |
| Heptamer | 0% by mass | 0% by mass | 4% by mass | 2% by mass | 4% by mass |
| Octamer | 0% by mass | 0% by mass | 2% by mass | 1% by mass | 3% by mass |
| Nonamer | 0% by mass | 0% by mass | 2% by mass | 1% by mass | 2% by mass |
| Decamer | 0% by mass | 0% by mass | 0% by mass | 0% by mass | 1% by mass |
| Undecamer | 0% by mass | 0% by mass | 0% by mass | 0% by mass | 1% by mass |
| Dodecamer | 0% by mass | 0% by mass | 0% by mass | 0% by mass | 0.4% by mass |
| Tridecamer | 0% by mass | 0% by mass | 0% by mass | 0% by mass | 0.2% by mass |
| Tetradecamer to eicosamer | 0% by mass | 0% by mass | 0% by mass | 0% by mass | 0% by mass |

TABLE 1-continued

| Total amount of trimer or higher order units/ (3HP + 3HP polymer) | 2.2% by mass | 10.6% by mass | 58.8% by mass | 46% by mass | 63% by mass |
|---|---|---|---|---|---|
| Methods for preparing material mixture from 16% by mass 3HP aqueous solution | | | Condensed with rotary evaporator (*4). | | |

(*1) Condensation was performed while the polymerization reaction was promoted, by heating the 3HP aqueous solution under reduced pressure using a 150° C. oil bath and a rotary evaporator for 5 hours, and removing water.
(*2) The 3HP aqueous solution was condensed by putting the 3HP aqueous solution in a thin-film evaporator (70° C. 3.3 kPa) while avoiding a polymerization reaction. The obtained bottom liquid was put again into the thin-film evaporator (76° C., 53 Pa), so that 3HP was obtained as a distillate. Water was added to the distillate, whereby and 80% bymass 3HP aqueous solution was obtained.
(*3) Storage was performed at 70° C. for 24 hours.
(*4) The condensation degrees were appropriately changed between the materials.

1. Example of First Aspect of the Present Invention

Example 1-1

A stainless steel tube with an inner diameter of 10 mm was filled with a stainless steel 1.5-mm Dixon packing, and the tube was set in an electric furnace. This system was used as a decomposition reactor. Another stainless steel tube with an inner diameter of 10 mm was filled with the above dehydration catalyst [crushed catalyst], and the tube was set in an electric furnace. This system was used as a dehydration reactor. The outlet of the decomposition reactor and the inlet of the dehydration reactor were connected with a stainless steel tube, so that the outlet gas from the decomposition reactor could be directly introduced into the dehydration reactor. An electric heater was used for heating around the connecting tube to prevent cooling of the gas in the connecting tube.

The temperature in the decomposition reactor was set to 375° C., and the temperature in the dehydration reactor was set to 300° C. The material 1-1, a composition containing a 3HP polymer, was supplied to the upper part of the decomposition reactor at a rate of 16.7 g/h. At the same time, nitrogen gas was supplied at a rate of 3 L/h. The outlet gas from the decomposition reactor was directly supplied to the dehydration reactor, and reacted continuously for 4 hours. The outlet gas from the dehydration reactor was collected by cooling, and the obtained reaction mixture was analyzed by liquid chromatography. 3HP and a polymer thereof were not detected, and the yield of the acrylic acid was 99 mol %.

Comparative Example 1-1

Example Using 3HP Monomer without Oligomerization (Polymerization)

The obtained material 1-2 was used as a material composition while the composition was cooled to 5° C. to minimize the formulation change, and the same dehydration reaction as in Example 1-1 was performed. The obtained reaction solution contained residual 3HP, and the yield of the acrylic acid was 81 mol %.

Example 1-1 showed a reduced amount of hydroxy groups because of the oligomerization, compared to Comparative Example 1-1. Hence, the load in the dehydration reaction was small, and thereby a high yield was achieved.

Example 1-2

The same dehydration reaction as in Example 1-1 was performed using the material 1-3. The yield of the acrylic acid was 91 mol %. Nitrogen in the reaction mixture was 18 ppm by mass based on the acrylic acid. The reaction solution was analyzed by gas chromatography, and no (meth)acrylamides was detected, being in an amount of 1 ppm by mass or less based on the acrylic acid.

Example 1-3

The same dehydration reaction as in Example 1-1 was performed using the material 1-4. The yield of the acrylic acid was 89 mol %. Nitrogen in the reaction mixture was 240 ppm by mass based on the acrylic acid. The reaction solution was analyzed by gas chromatography, and (meth)acrylamides were detected, being in an amount of 25 ppm by mass based on the acrylic acid. The large amount of nitrogen in the material led to the increase in the amount of nitrogen and the amount of (meth)acrylamides in the reaction solution.

Example 1-4

The material 1-1 (5 g) was charged into a stainless steel reactor that included a feed tube for the starting material and gas, an extraction tube for the generated vapor component and the supplied gas, and a back pressure valve provided to the extraction tube, and was adjusted to have an internal pressure of 103 kPa (gauge pressure). The reactor was put into an oil bath such that the internal temperature was increased to 250° C. The material 1-1 was supplied to the reactor at a rate of 18.5 g/h, and nitrogen gas was supplied to the reactor at a rate of 6 L/h. At the same time, the generated vapor component and nitrogen gas were extracted through the gas extraction tube of the reactor. The extracted vapor component was collected by cooling, whereby a reaction solution was obtained. The reaction was continuously performed until a certain amount of liquid was present in the reactor and the balance between the amount of the material and the amount of the product was stable. The reaction solution obtained during stable reaction was analyzed. The yield of the acrylic acid was 81 mol %.

Using a rotary evaporator, water and acrylic acid were distilled off from the obtained reaction solution. The residual component contained 3HP, 3HP dimer, acrylic acid, and acrylic acid dimer. The residual component (10 g) was added to the aqueous solution (300 g) of 3HP having a concentration of 16% by mass obtained in the above (Preparation 1 of material 3HP), and the mixture was concentrated with a rotary evaporator. The formulation of the obtained concentrated product is shown in Table 2.

TABLE 2

| | |
|---|---|
| H₂O | 24% by mass |
| 3HP | 26% by mass |

TABLE 2-continued

| | |
|---|---|
| 3HP dimer | 22% by mass |
| 3HP trimer | 13% by mass |
| 3HP tetramer | 7% by mass |
| 3HP pentamer | 4% by mass |
| 3HP hexamer | 2% by mass |
| 3HP heptamer | 1% by mass |
| 3HP octamer | 0.5% by mass |
| 3HP nonamer | 0.3% by mass |
| Acrylic acid | 0.2% by mass |
| Acrylic acid dimer | 0.4% by mass |
| Acrylic acid trimer | 0.5% by mass |
| Total amount of 3HP trimer or higher order units/(3HP + 3HP polymer) | 37% by mass |

With the concentrated product as a starting material, reaction was performed under the same conditions as described above. The reaction solution obtained during stable reaction was analyzed. The yield of the acrylic acid was 80 mol %.

Example 1-5

Purification of Acrylic Acid Through Crystallization

The aqueous solution of acrylic acid obtained in Example 1-1 was distilled, and a crude acrylic acid containing 88.2% by mass of acrylic acid was obtained from the bottom. The crude acrylic acid as a mother liquid was cooled to a temperature in the range of room temperature (about 20° C.) to −5.7° C. to deposit crystals. The crude acrylic acid was held at the same temperature, and crystallized to isolate the crystals from the liquid by suction filtration. The isolated crystals were melt, and part of the melt was sampled for analysis. The residual part was used as a mother liquid and cooled to a temperature in the range of room temperature (about 20° C.) to 4.9° C. to deposit crystals. The mother liquid was held at the same temperature, and crystallized to isolate the crystals from the liquid by suction filtration. The crystallization performed twice provided a purified acrylic acid. The purity of the acrylic acid was 99.9% or higher.
(Production of Water-Absorbing Resin)

To the purified acrylic acid obtained above, 60 ppm by mass of p-methoxy phenol was added as a polymerization inhibitor. Separately, a mixture of acrylic acid and the above polymerization inhibitor was added with cooling (liquid temperature: 35° C.) to an NaOH aqueous solution obtained from sodium hydroxide containing 0.2 ppm by mass of iron, so that the solution was neutralized to 75 mol %. The resulting sodium acrylate aqueous solution had a degree of neutralization of 75 mol % and a concentration of 35% by mass. In the aqueous solution, polyethylene glycol diacrylate (0.05 mol % based on sodium acrylate aqueous solution) as an internal cross-linking agent was dissolved. Thereby, a monomeric component was obtained. The monomeric component (300 g) was put into a 1-L cylindrical vessel, and nitrogen gas was blown into the vessel at a rate of 2 L/min. Then, the vessel was deaerated for 20 minutes. Subsequently, an aqueous solution of sodium persulfate (0.10 g/mol based on the monomeric component) and L-ascorbic acid (0.004 g/mol based on the monomeric component) was added to the vessel with stirring using a stirrer, so that the polymerization was started. The stirring was stopped after the start of the polymerization, and standing aqueous polymerization was performed. The monomeric component was observed to have a peak polymerization temperature of 106° C. about 15 minutes later (polymerization peak time). Then, the polymerization was allowed to proceed for 30 minutes. The polymer was then taken out of the cylindrical vessel, whereby a hydrous gel-type cross-linked polymer was obtained. The obtained hydrous gel-type cross-linked polymer was fractioned by a meat chopper (pore size: 8 mm) at 45° C., and then heated to dryness by a 170° C. hot air dryer for 20 minutes. Also, the dried polymer (solids content: about 95%) was ground by a roll mill, and the resulting powder was classified into particle sizes of 600 to 300 μm using a JIS standard sieve, so that a polyacrylic acid water-absorbing resin (degree of neutralization: 75%) was obtained.

The polymerizability of the acrylic acid obtained by the method for producing acrylic acid of the present invention was equivalent to the polymerizability of acrylic acid obtained by the method for producing acrylic acid using propylene as a starting material. The obtained water-absorbing resin had no odor, and had equivalent physical properties.

A 3HP solution tends to be polymerized with time to cause a change in the formulation and the physical properties such as viscosity, and thus is unsuitable for use in an industrial method. In order to minimize the change in the formulation, operations and instruments for cooling the 3HP solution, for example, are required, which increases the cost. Accordingly, from the viewpoint of applying a 3HP solution to an industrial production method, it is important to use an oligomer of 3HP, not a monomer solution of 3HP, as described herein.

In this way, the effect of achieving enhanced productivity or reduction in the amount of a catalyst in production of (meth)acrylic acid from a composition containing a 3-hydroxycarboxylic acid polymer, and enabling stable production of the (meth)acrylic acid at low cost is considered to be always provided if the method is used which is for producing (meth)acrylic acid using 3-hydroxycarboxylic acid as a starting material, the method including a polymerization step of polymerizing 3-hydroxycarboxylic acid to generate a composition containing a 3-hydroxycarboxylic acid polymer, and a step of generating (meth)acrylic acid from the composition containing the 3-hydroxycarboxylic acid polymer, the 3-hydroxycarboxylic acid polymer obtained in the polymerization step including trimer or higher order units, the trimer or higher order units constituting 3% by mass or more of a total of 100% by mass of the 3-hydroxycarboxylic acid and the 3-hydroxycarboxylic acid polymer.

If the 3-hydroxycarboxylic acid polymer obtained through the polymerization step includes trimer or higher order units that constitute 3% by mass or more of a total of 100% by mass of the 3-hydroxycarboxylic acid and the 3-hydroxycarboxylic acid polymer, the structure achieves a significant effect for long-term, stable reaction of the starting material for producing a large amount of the (meth)acrylic acid.

The step of generating (meth)acrylic acid from the composition containing a 3-hydroxycarboxylic acid polymer preferably includes the step of performing the dehydration step using a dehydration catalyst.

In the case of generating (meth)acrylic acid by heating without the dehydration step using a dehydration catalyst or in the case that unreacted 3-hydroxycarboxylic acid, a polymer thereof, and a (meth)acrylic acid polymer remain, the residues are preferably recycled for the polymerization step or the step of generating (meth)acrylic acid.

Therefore, the results of the examples show that the first aspect of the present invention is applicable to the whole technical range of the first aspect of the present invention or to the various embodiments described herein, and that the advantageous effects are achieved.

2. Example of Second Aspect of the Present Invention Example 2-1

A stainless steel reaction tube with an inner diameter of 10 mm was filled with γ-alumina as a dehydration catalyst. On the γ-alumina, a 1.5-mm stainless steel Dixon packing was stacked as an evaporation layer. The reaction tube was heated to 350° C. in an electric furnace, and the above material 2-2 was supplied to the upper part of the reaction tube at a rate of 4.0 g/h. At the same time, nitrogen gas was blown into the tube at a rate of 3 L/h.

The reaction gas extracted from the bottom of the reaction tube was collected by cooling, so that a reaction solution was obtained. The reaction solution obtained was analyzed by liquid chromatography. The yield of the acrylic acid was 92 mol %. The concentration of the acrylic acid in the reaction solution was 37% by mass.

The latent heat of evaporation of water contained in the material 2-2 was calculated to be 3217 J per gram of the generated acrylic acid (calculated with a value of the latent heat of evaporation of water at 100° C. of 2265 J/g).

Comparative Example 2-1

The same process as in Example 2-1 was carried out, except that the material 2-2 was changed to the material 2-1 and the feed rate of the material was set to 8.4 g/h. The feed rate of the starting material was set such that the number of moles of the 3HP units supplied per unit time was the same. Analysis on the collected reaction solution gave a yield of the acrylic acid of 92 mol %. The concentration of the acrylic acid in the reaction solution was 18% by mass. The latent heat of evaporation of water contained in the material 2-1 was calculated to be 9806 J per gram of the generated acrylic acid. The amount of heat required in evaporation of water was 3 times that in Example 2-1. In vapor phase reaction, the proportion of the energy cost is high in the production cost, and in particular, the proportion of the energy required for evaporation of the starting materials is very high. Hence, in the case of using a starting material with a small amount of trimer to eicosamer of 3HP and large amounts of low molecular component and water, such as the material 2-1, the production cost is very high.

Comparative Example 2-2

The same process as in Example 2-1 was carried out, except that the material 2-2 was changed to the material 2-4 and the feed rate of the material was set to 3.2 g/h. The feed rate of the material 2-4 was set such that the number of moles of the 3HP units supplied per unit time was the same. Analysis on the collected reaction solution gave a yield of the acrylic acid of 71 mol %. In this way, in the case of using as a starting material a 3HP polymer having a high molecular weight with a small amount of trimer to eicosamer of 3HP, such as the material 2-4, the yield of the acrylic acid greatly decreased.

Example 2-2

The same process as in Example 2-1 was carried out, except that the material 2-2 was changed to the material 2-3 and the feed rate of the material was set to 2.0 g/h. The feed rate of the material was set such that the number of moles of the 3HP units supplied per unit time was the same. Analysis on the collected reaction solution gave a yield of the acrylic acid of 90 mol %. The concentration of the acrylic acid in the reaction solution was 71% by mass.

Example 2-3

A stainless steel reaction tube with an inner diameter of 10 mm was filled with a stainless steel 1.5-mm Dixon packing only, and the reaction was performed in the absence of a catalyst. The reaction tube was heated to 400° C. in an electric furnace, and the above material 2-3 was supplied to the upper part of the reaction tube at a rate of 2.0 g/h. At the same time, nitrogen gas was blown into the tube at a rate of 3 L/h.

The reaction gas extracted from the bottom of the reaction tube was collected by cooling, so that a reaction solution was obtained. The reaction solution obtained was analyzed by liquid chromatography. The concentration of the acrylic acid in the reaction solution was 39% by mass.

Comparative Example 2-3

The same process as in Example 2-3 was carried out, except that the material 2-3 was changed to the material 2-1 and the feed rate of the material was set to 8.4 g/h. The feed rate of the material was set such that the number of moles of the 3HP units supplied per unit time was the same. The collected reaction solution was analyzed. The concentration of the acrylic acid in the reaction solution was 9% by mass.

Example 2-4

The material 2-3 (5 g) was charged into a stainless steel reactor that included a feed tube for the material and gas, and an extraction tube for the generated vapor component and the supplied gas. The reactor was put into an oil bath such that the internal temperature was increased to 250° C. The material 2-3 was supplied to the reactor at a rate of 25.6 g/h, and nitrogen gas was supplied to the reactor at a rate of 6 L/h. At the same time, the generated vapor component and nitrogen gas were extracted through the gas extraction tube of the reactor. The extracted vapor component was collected by cooling, whereby a reaction solution was obtained. The reaction was continuously performed until a certain amount of liquid was present in the reactor and the balance between the amount of the material and the amount of the product was stable. The reaction solution obtained during stable reaction was analyzed. The yield of the acrylic acid was 70 mol %.

Example 2-5

Purification of Acrylic Acid Through Crystallization

The aqueous solution of acrylic acid obtained in Example 2-2 was purified through crystallization of the acrylic acid in the same manner as in Example 1-5, so that a purified acrylic acid was obtained. The purity of the acrylic acid was 99.9% or higher.

(Production of Water-Absorbing Resin)

The purified acrylic acid obtained as described above was used to perform the method for producing a water-absorbing resin in the same manner as in Example 1-5, whereby a polyacrylic acid water-absorbing resin (degree of neutralization: 75%) was obtained.

The polymerizability of the acrylic acid obtained by the method for producing acrylic acid of the present invention was equivalent to the polymerizability of acrylic acid obtained by the method for producing acrylic acid using propylene as a starting material. The obtained water-absorbing resin had no odor, and had equivalent physical properties.

The above results show that acrylic acid can be produced with a high yield and at low cost in Examples 2-1 to 2-4 each employing a material composition in which the total amount of trimer to eicosamer of the 3-hydroxycarboxylic acid polymer was 10% by mass or more of a total of 100% by mass of the 3-hydroxycarboxylic acid and the 3-hydroxycarboxylic acid polymer. If the obtained composition contains 3-hydroxycarboxylic acid, a polymer represented by the formula (2), or a polymer represented by the formula (3) remained, the 3-hydroxycarboxylic acid and the polymers after separation of the acrylic acid in the purification step are preferably reused as starting materials in the polymerization step and the heating step. Thereby, the yield of the acrylic acid can be further improved. Example 2-3 and Example 2-4 in each of which the dehydration step was not performed gave a favorable yield of the acrylic acid which, however, is lower than the yield in Example 2-1 or Example 2-2. In the case of performing only the heating step and excluding the dehydration step with a dehydration catalyst as in the case of Example 2-3 and Example 2-4, the 3-hydroxycarboxylic acid and the polymers are particularly preferably reused as starting materials in the polymerization step and the heating step. Thereby, the effect of increasing the yield of acrylic acid would be significant.

Example 2-5 proved that the acrylic acid obtained in Example 2-2 had the polymerizability equivalent to that of acrylic acid obtained by the method for producing acrylic acid using propylene as a starting material, and that a water-absorbing resin with no odor and with excellent physical properties can be produced using the acrylic acid obtained in Example 2-2. In contrast, Comparative Examples 2-1 to 2-3 each using a material composition failing to satisfy the above conditions showed a decrease in the yield of acrylic acid or a significant increase in the production cost.

In this way, the effect of achieving low cost and suppression of clogging in the reactor or the like instruments and a decrease in the catalytic activity, and enabling long term, stable production of the (meth)acrylic acid with a high yield is considered to be always provided if the method for producing (meth)acrylic acid from a material composition containing a 3-hydroxycarboxylic acid polymer is used in which trimer to eicosamer in the 3-hydroxycarboxylic acid polymer constitute 10% by mass or more of a total of 100% by mass of the 3-hydroxycarboxylic acid and the 3-hydroxycarboxylic acid polymer, and the (meth)acrylic acid generation step includes heating the composition to generate (meth)acrylic acid.

Therefore, the results of the examples show that the second aspect of the present invention is applicable to the whole technical range of the second aspect of the present invention or to the various embodiments described herein, and that the advantageous effects are achieved.

3. Example of Third Aspect of the Present Invention

Example 3-1

A stainless steel tube with an inner diameter of 10 mm was filled with a stainless steel 1.5-mm (outer diameter) Dixon packing, and the tube was set in an electric furnace. This system was used as a decomposition reactor. Another stainless steel tube with an inner diameter of 10 mm was filled with γ-alumina as a dehydration catalyst, and the tube was set in an electric furnace. This system was used as a dehydration reactor. The outlet of the decomposition reactor and the inlet of the dehydration reactor were connected with a stainless steel tube, so that the outlet gas from the decomposition reactor could be directly introduced into the dehydration reactor. An electric heater was used for heating around the connecting tube to prevent cooling of the gas in the connecting tube.

The temperature in the decomposition reactor was set to 375° C., and the temperature in the dehydration reactor was set to 300° C. The material 3-1 as a material solution was supplied to the upper part of the decomposition reactor at a rate of 2.2 g/h. At the same time, nitrogen gas was supplied at a rate of 7 L/h. The outlet gas from the decomposition reactor was directly supplied to the dehydration reactor, and reacted continuously for 8 hours. The outlet gas from the dehydration reactor was collected by cooling, and the obtained reaction mixture was analyzed by liquid chromatography. The yield of the acrylic acid was 92 mol %. Trimer or higher order oligomer was not detected in the reaction solution.

Example 3-2

In Example 3-1, the outlet gas from the decomposition reactor was not supplied to the dehydration reactor, and was directly collected by cooling. The reaction solution collected was analyzed by liquid chromatography. The yield of the acrylic acid was 53 mol %. The formulation thereof is shown in Table 3. The results in Table 3 show that the polymer of the material solution was decomposed in the decomposition reactor.

TABLE 3

| | |
|---|---|
| $H_2O$ | 26% by mass |
| 3HP | 21% by mass |
| 3HP dimer | 2% by mass |
| Acrylic acid | 39% by mass |
| Acrylic acid dimer | 11% by mass |
| Acrylic acid trimer | 2% by mass |

Examples 3-3

In Example 3-1, the material solution was directly supplied to the dehydration reactor without being introduced into the decomposition reactor. One hour later, the reaction was stopped because the internal pressure of the dehydration reactor increased rapidly. After cooling, in the dehydration reactor, a large amount of brown accumulated product was observed on the catalyst layer, which caused clogging in the reaction tube. Analysis on the reaction solution obtained before the clogging gave a yield of the acrylic acid of 80 mol %.

Examples 3-4

The decomposition step using a decomposition reactor and the dehydration reaction step using a dehydration reactor were performed in the same manner as in Example 3-1 except for the following changes. That is, the decomposition step using a decomposition reactor and the dehydration reaction step using a dehydration reactor were performed in the same manner as in Example 3-1 except that the inner diameter of the stainless steel tube constituting the decomposition reactor was changed to 22 mm, the outer diameter of the Dixon packing charged into the decomposition reactor was changed to 3 mm, the dehydration catalyst used for the dehydration reactor was the above molded catalyst, the temperature in the decomposition reactor was 300° C., the material 3-2 was supplied as a starting material to the upper part of the decomposition reactor at a rate of 18 g/h, and at the same time, nitrogen gas was supplied at a rate of 1.8 L/h.

The outlet gas from the dehydration reactor was collected by cooling, and the obtained reaction mixture was analyzed by liquid chromatography. 3HP and a polymer thereof were not detected, and the yield of the acrylic acid was 97 mol %.

The polymerizability of the acrylic acid obtained by the method for producing acrylic acid of the present invention was equivalent to the polymerizability of acrylic acid obtained by the method for producing acrylic acid using propylene as a starting material. The obtained water-absorbing resin had no odor, and had equivalent physical properties.

The above results show that Example 1-1, Example 1-2, Example 1-4, and Example 3-1 to Example 3-4 achieved a high yield of the acrylic acid. Especially Example 1-1, Example 1-2, Example 3-1, and Example 3-4 in which the two-stage reaction including the decomposition step and the dehydration step was conducted allowed suitable production of acrylic acid with a high yield. Example 1-3 also employed the two-stage reaction including the decomposition step and the dehydration step, and achieved a high yield of the acrylic acid. In this example, however, a large amount of nitrogen was contained in the material, and as a result, the amount of nitrogen and the amount of (meth)acrylamides in the reaction solution increased. In Example 1-4, (meth)acrylic acid was generated by heating without the dehydration step using a dehydration catalyst. Here, the impurities that can be the starting materials of the (meth)acrylic acid were recycled as starting materials in the polymerization step, so that acrylic acid was suitably produced using the impurities. If the obtained composition contained 3-hydroxycarboxylic acid, a 3-hydroxycarboxylic acid polymer represented by the formula (2), and a (meth)acrylic acid polymer represented by the formula (3), the 3-hydroxycarboxylic acid and the polymers after separation of the acrylic acid in the purification step are preferably reused as starting materials in the polymerization step, the decomposition step, and the dehydration step. Thereby, the yield of acrylic acid can be further increased. Example 3-2 in which the dehydration step was not performed gave a favorable yield of acrylic acid which, however, is lower than the yield in Example 3-1. In the case of performing only the decomposition step and excluding the dehydration step with a dehydration catalyst as in the case of Example 3-2, the 3-hydroxycarboxylic acid and the polymers are particularly preferably reused as the starting materials in the polymerization step and the decomposition step. Thereby, the effect of increasing the yield of acrylic acid would be significant.

Example 1-5 proved that the acrylic acid obtained in Example 1-1 had the polymerizability equivalent to that of the acrylic acid obtained by the method for producing acrylic acid using propylene as a starting material, and that a water-absorbing resin with no odor and with excellent physical properties can be produced using the acrylic acid obtained in Example 1-1.

In this way, the effect of achieving suppression of clogging in the reactor or the like instruments and a decrease in the catalytic activity, and enabling long term, stable production of the (meth)acrylic acid with a high yield is considered to be always provided if the method for producing (meth)acrylic acid from a material composition containing a 3-hydroxycarboxylic acid polymer is used which includes (a) a decomposition step of generating a decomposed product of the 3-hydroxycarboxylic acid polymer, and (b) a dehydration step of generating (meth)acrylic acid by bringing the decomposed product into contact with a dehydration catalyst.

Therefore, the results of the examples show that the third aspect of the present invention is applicable to the whole technical range of the third aspect of the present invention or to the various embodiments described herein, and that the advantageous effects are achieved.

The invention claimed is:

1. A method for producing (meth)acrylic acid using 3-hydroxycarboxylic acid as a starting material, the method comprising:
   a polymerization step of polymerizing 3-hydroxycarboxylic acid so as to generate a composition comprising a 3-hydroxycarboxylic acid polymer; and
   a step of generating (meth)acrylic acid from the composition comprising the 3-hydroxycarboxylic acid polymer,
   wherein the 3-hydroxycarboxylic acid polymer obtained in the polymerization step comprises trimer or higher order units,
   trimer to eicosamer units present in the 3-hydroxycarboxylic acid polymer constitute an amount in a range of 10% by mass or more relative to a total amount of the 3-hydroxycarboxylic acid and the 3-hydroxycarboxylic acid polymer as 100% by mass, and
   the (meth)acrylic acid generation step comprises heating the composition so as to generate (meth)acrylic acid.

2. The production method according to claim 1, further comprising a fermentation step,
   wherein through the fermentation step, the 3-hydroxycarboxylic acid used as the starting material is generated.

3. The production method according to claim 1,
   wherein the 3-hydroxycarboxylic acid is 3-hydroxypropionic acid.

4. The production method according to claim 1,
   wherein the (meth)acrylic acid generation step comprises:
   (a) a decomposition step of generating a decomposed product of the 3-hydroxycarboxylic acid polymer; and
   (b) a dehydration step of generating (meth)acrylic acid by bringing the decomposed product into contact with a dehydration catalyst.

5. The production method according to claim 4,
   wherein the decomposition step is performed by heating.

6. A method for producing (meth)acrylic acid using 3-hydroxycarboxylic acid as a starting material, the method comprising:
   a polymerization step of polymerizing 3-hydroxycarboxylic acid so as to generate a composition comprising a 3-hydroxycarboxylic acid polymer; and
   a step of generating (meth)acrylic acid from the composition comprising the 3-hydroxycarboxylic acid polymer,
   wherein the (meth)acrylic acid generation step comprises:
   (a) a decomposition step of generating a decomposed product of the 3-hydroxycarboxylic acid polymer; and
   (b) a dehydration step of generating (meth)acrylic acid by bringing the decomposed product into contact with a dehydration catalyst.

7. A composition containing (meth)acrylic acid, obtainable by the production method according to claim 1,
wherein an amount of a nitrogen-containing compound in the composition is 80 ppm by mass or less as an amount of nitrogen relative to the (meth)acrylic acid.

8. A method for producing a hydrophilic resin using 3-hydroxycarboxylic acid as a starting material, the method comprising:
a first polymerization step of polymerizing 3-hydroxycarboxylic acid so as to generate a composition comprising a 3-hydroxycarboxylic acid polymer;
a step of generating (meth)acrylic acid from the composition comprising the 3-hydroxycarboxylic acid polymer; and
a second polymerization step of polymerizing a monomeric component comprising the (meth)acrylic acid so as to generate a hydrophilic resin,
wherein the 3-hydroxycarboxylic acid polymer obtained in the first polymerization step comprises trimer or higher order units,
trimer to eicosamer units present in the 3-hydroxycarboxylic acid polymer constitute an amount in a range of 10% by mass or more relative to a total amount of the 3-hydroxycarboxylic acid and the 3-hydroxycarboxylic acid polymer as 100% by mass, and
the (meth)acrylic acid generation step comprises heating the composition so as to generate (meth)acrylic acid.

9. The production method according to claim 8,
wherein the (meth)acrylic acid generation step comprises:
(a) a decomposition step of generating a decomposed product of the 3-hydroxycarboxylic acid polymer; and
(b) a dehydration step of generating (meth)acrylic acid by bringing the decomposed product into contact with a dehydration catalyst.

10. The method according to claim 8,
wherein the hydrophilic resin is a water-absorbing resin.

11. A composition containing a hydrophilic resin, obtainable by the production method according to claim 8,
wherein an amount of a nitrogen-containing compound in the composition is 80 ppm by mass or less as an amount of nitrogen relative to the hydrophilic resin.

12. A composition containing (meth)acrylic acid, obtainable by the production method according to claim 6,
wherein an amount of a nitrogen-containing compound in the composition is 80 ppm by mass or less as an amount of nitrogen relative to the (meth)acrylic acid.

13. The production method according to claim 6, further comprising a fermentation step,
wherein through the fermentation step, the 3-hydroxycarboxylic acid used as the starting material is generated.

14. The production method according to claim 6,
wherein the 3-hydroxycarboxylic acid is 3-hydroxypropionic acid.

15. The production method according to claim 6,
wherein trimer to eicosamer units present in the 3-hydroxycarboxylic acid polymer constitute an amount in a range of 10% by mass or more relative to a total amount of the 3-hydroxycarboxylic acid and the 3-hydroxycarboxylic acid polymer as 100% by mass, and
the (meth)acrylic acid generation step comprises heating the composition so as to generate (meth)acrylic acid.

16. The production method according to claim 6,
wherein the decomposition step is performed by heating.

17. A method for producing a hydrophilic resin using 3-hydroxycarboxylic acid as a starting material, the method comprising:
a first polymerization step of polymerizing 3-hydroxycarboxylic acid so as to generate a composition containing a 3-hydroxycarboxylic acid polymer,
a step of generating (meth)acrylic acid from the composition comprising the 3-hydroxycarboxylic acid polymer, and
a second polymerization step of polymerizing a monomeric component comprising the (meth)acrylic acid so as to generate a hydrophilic resin,
the (meth)acrylic acid generation step comprising
(a) a decomposition step of generating a decomposed product of the 3-hydroxycarboxylic acid polymer, and
(b) a dehydration step of generating (meth)acrylic acid by bringing the decomposed product into contact with a dehydration catalyst.

18. The production method according to claim 17,
wherein the hydrophilic resin is a water-absorbing resin.

19. The production method according to claim 17,
wherein an amount of a nitrogen-containing compound in the composition is 80 ppm by mass or less as an amount of nitrogen relative to the hydrophilic resin.

* * * * *